United States Patent [19]

Companion et al.

[11] Patent Number: 5,282,472
[45] Date of Patent: Feb. 1, 1994

[54] SYSTEM AND PROCESS FOR THE DETECTION, EVALUATION AND TREATMENT OF PROSTATE AND URINARY PROBLEMS

[76] Inventors: John A. Companion, 20A Curtis La., Hampton, Va. 23669; Bobby G. Batten, 19 Terrell Rd., Newport News, Va. 23606

[21] Appl. No.: 62,617

[22] Filed: May 11, 1993

[51] Int. Cl.⁵ .................. A61B 8/12; A61B 17/00
[52] U.S. Cl. .................. 128/662.06; 128/7; 606/108; 623/12
[58] Field of Search .............. 128/660.03, 662.06, 128/7; 606/108, 198; 600/3; 623/1, 12

[56] References Cited

U.S. PATENT DOCUMENTS

| | | | |
|---|---|---|---|
| 4,561,446 | 12/1985 | Hetz | 128/7 X |
| 4,665,918 | 5/1987 | Garza et al. | 623/12 |
| 4,681,570 | 7/1987 | Dalton | 604/282 |
| 4,795,458 | 1/1991 | Regan | 623/1 |
| 4,990,151 | 2/1991 | Wallsten | 606/108 |
| 4,994,066 | 2/1991 | Voss | 606/108 |
| 5,026,377 | 6/1991 | Burton et al. | 606/108 |
| 5,049,132 | 9/1991 | Shaffer et al. | 604/101 |
| 5,078,720 | 1/1992 | Burton et al. | 606/108 |
| 5,098,374 | 3/1992 | Othel-Jacobsen et al. | 606/108 X |
| 5,107,844 | 4/1992 | Kami et al. | 128/662.06 |
| 5,147,370 | 9/1992 | McNamara | 606/108 |
| 5,159,920 | 11/1992 | Condon et al. | 128/662.06 X |
| 5,160,341 | 11/1992 | Brenneman | 606/198 |
| 5,163,952 | 11/1992 | Froix | 623/1 |
| 5,178,148 | 1/1993 | Lacoste et al. | 128/662.06 X |
| 5,192,297 | 3/1993 | Hull | 606/108 X |

OTHER PUBLICATIONS

Widron, J. et al. "Continuous Flow Urological Endoscopic Apparatus", WO82/03545 Published Intnl Applen, Oct. 1982.

*Primary Examiner*—Francis Jaworski
*Attorney, Agent, or Firm*—Wallace J. Nelson

[57] ABSTRACT

A compound system and process for mapping the urethra of a male patient to detect prostate and urinary problems; evaluation of any problems found; a reinforcement insert for the prostate custom fabricated from the mapped data to alleviate any problems found; means for placing the reinforcement insert into position within the patient; and means for removing the reinforcement insert when needed; are disclosed.

49 Claims, 9 Drawing Sheets

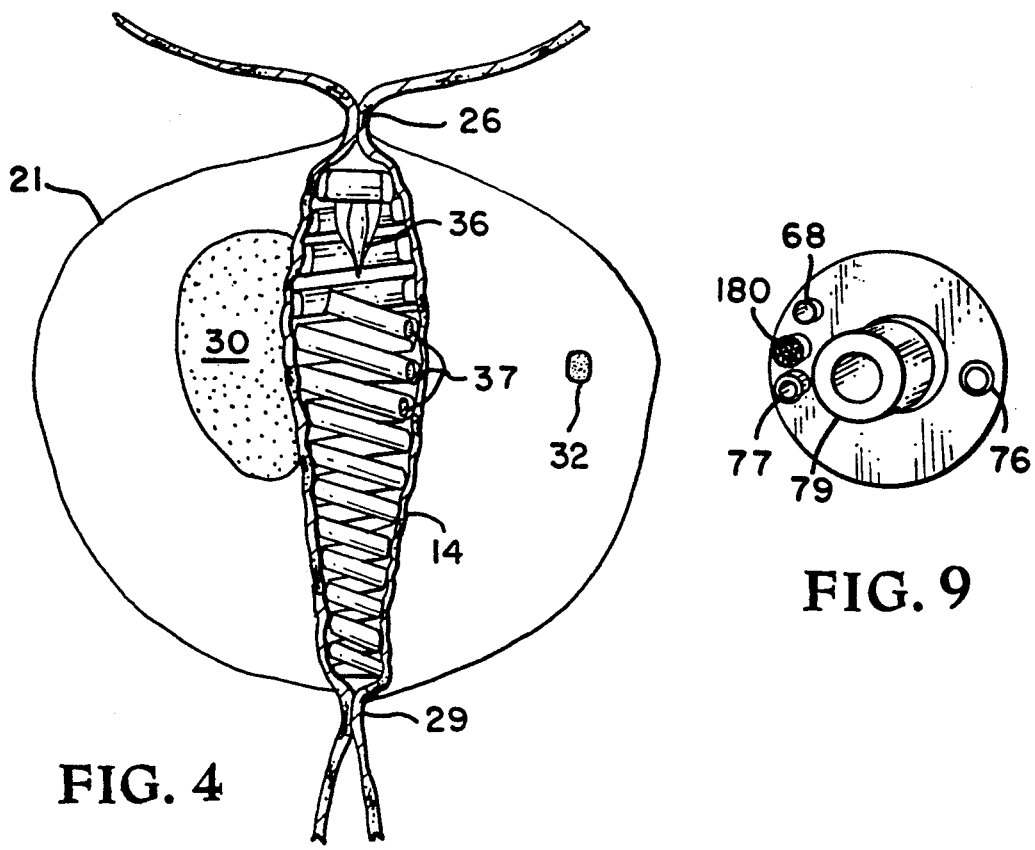
FIG. 4
FIG. 9
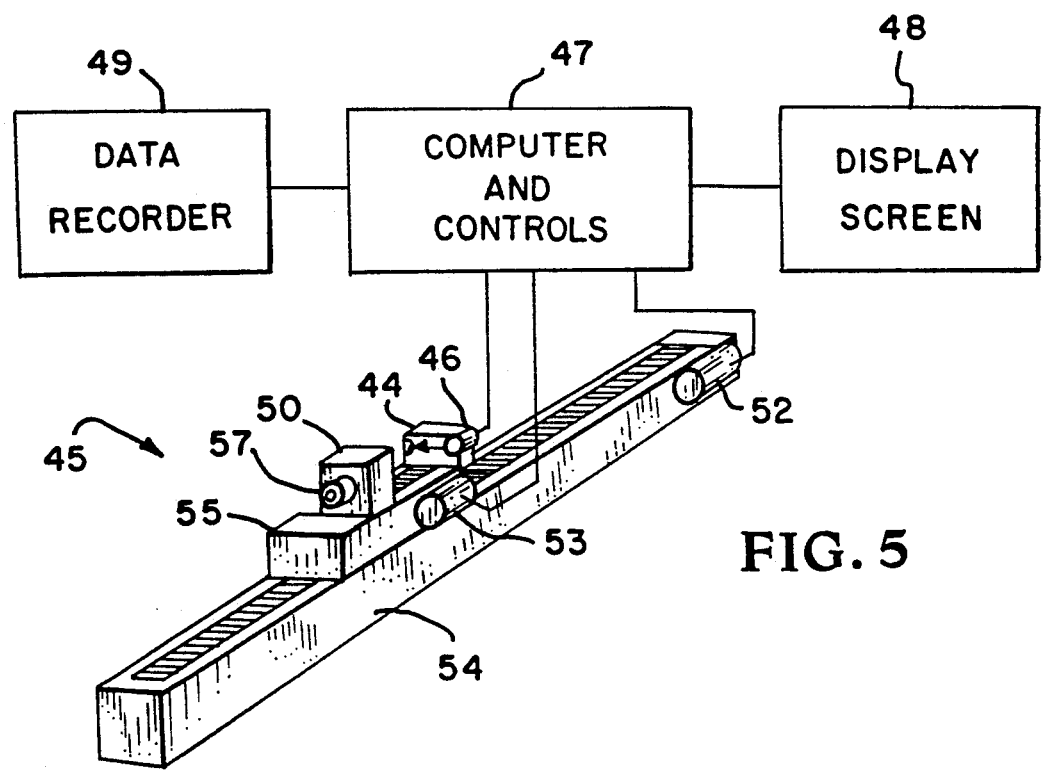
FIG. 5

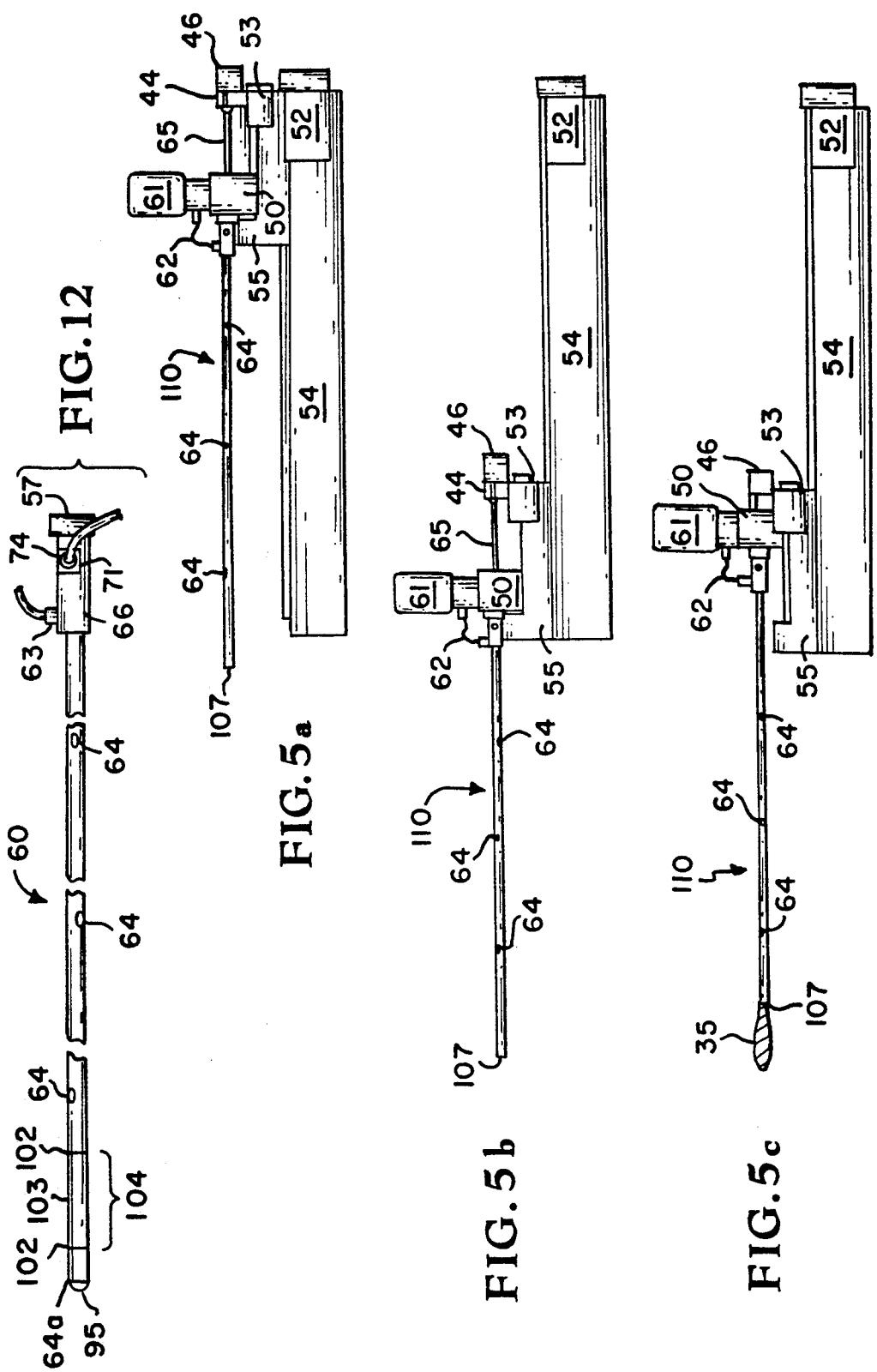

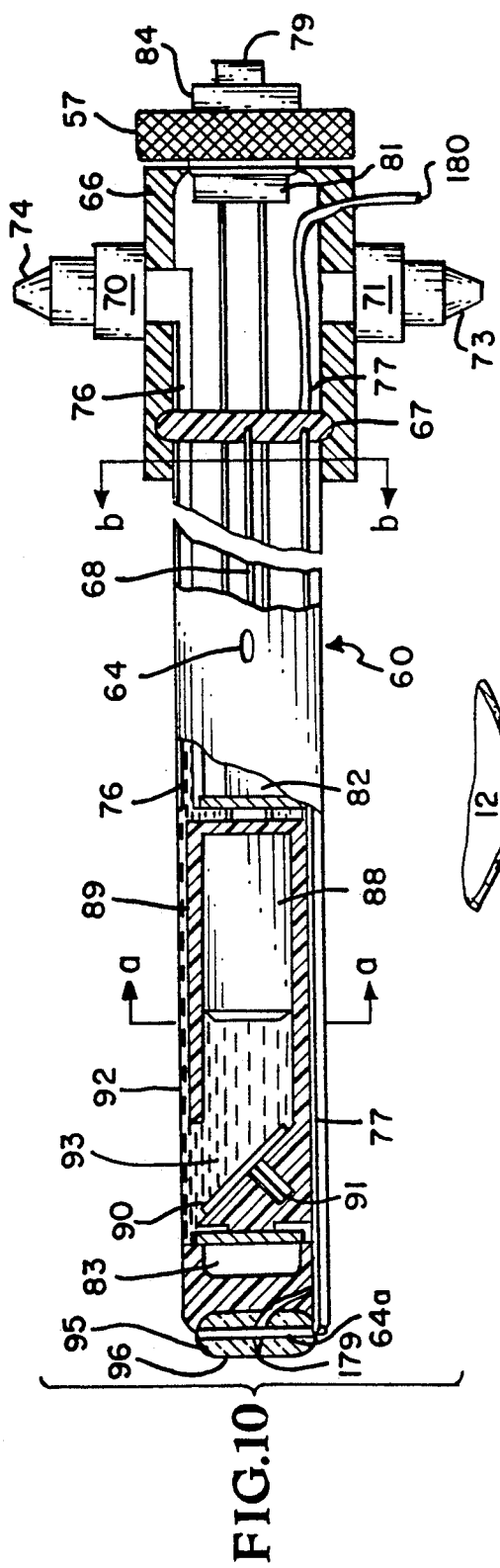
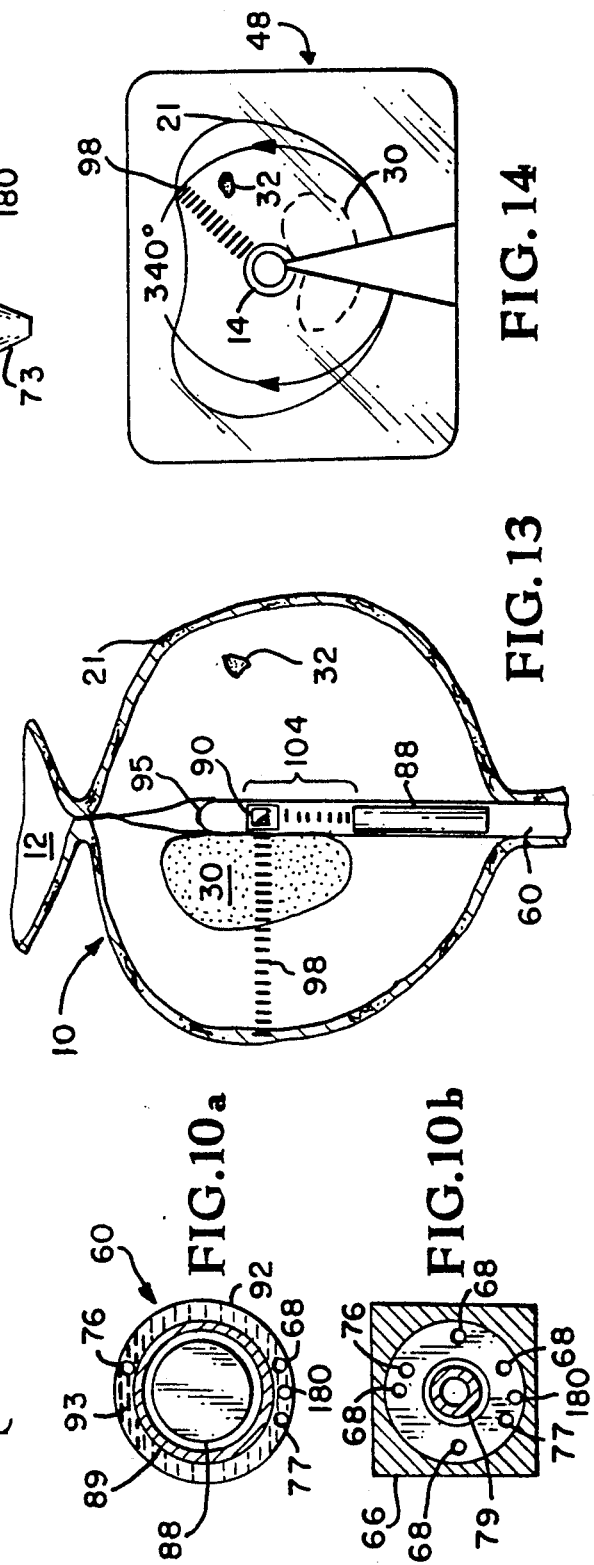

SYSTEM AND PROCESS FOR THE DETECTION, EVALUATION AND TREATMENT OF PROSTATE AND URINARY PROBLEMS

FIELD OF THE INVENTION

This invention relates generally to medical devices and relates specifically to a system and process for detecting, evaluating and treatment of prostate and urinary problems.

BACKGROUND OF THE INVENTION

The prostate is unique to the male of the species and consists of a mass of highly glandular tissue located just below the urinary bladder. The urethra exits the bottom of the bladder via a short neck which connects with the prostate. The prostate is bounded at the top by the involuntary sphincter and at the bottom by the voluntary sphincter and serves an important role in the production of seminal fluid during intercourse. The shape of the prostate has been compared to a chestnut, or a small turnip. It has a normal diameter of an inch and a half, and about an inch in length from top to bottom. The prostate consists primarily of numerous small glands that are bunched together in two large lateral lobes and a smaller middle lobe.

In cross section, the prostate normally shows a triangular arrangement with the two lateral lobes, appearing almost circular in section, lying on either side of the urethra on the side closest to the rectal wall, and a middle lobe being smaller and nestling between the lateral lobes on the front side of the prostate. The entire organ is encased in a tough muscular sheath, and is attached via a short neck to the base of the urinary bladder. The neck passes through a sheet of muscle, forming the involuntary sphincter, that underlies the fascia covering the bottom of the abdominal cavity. The bladder lies above the fascia within the abdominal cavity, and the prostate lies just below that fascia. As the urethra leaves the prostate it passes through another sheet of muscle, which forms the voluntary sphincter, and then into the penis. The retention of urine in the bladder is controlled by the two sphincters, voluntary and involuntary. The involuntary sphincter is the primary mechanism responsible for continence as it constricts the urethra and prevents the leakage of urine at volumes too low to be noticeable by the individual and during sleep. The voluntary sphincter acts as a secondary backup when there is a large quantity of urine. Urination is effected by a relaxation of both the sphincters combined with muscular contraction of the bladder and aided by gravity.

It has been estimated that, with advancing age, as many as 80% of all men will be affected by prostate problems. The primary prostate problem encountered is enlargement of the prostate, or Benign Prostatic Hyperplasia (BPH). The symptoms of BPH start with difficulty in voiding, difficulty in voiding completely, frequent urination (interruption of sleep), urinary tract infections from pooling of the urine, and can progress to over distention of the bladder, and kidney failure. In an individual suffering from BPH, excess tissue growth within the prostate applies pressure to the urethra, constricting the normal flow of urine, potentially to the point of complete blockage.

In this situation, muscular contraction of the bladder cannot overcome the constriction to force the urine through, because of the nature of the mechanical relationship of the bladder and the prostate. When the bladder contracts, it pulls down toward the base. Because it is anchored only at the base, it pulls against that anchor. The prostate is, in effect, that anchor. Normally, both sphincters relax, there is no constriction of the urethra, and the urine flows. However, when BPH is present, it acts like a sphincter which never relaxes. Therefore, the pressure generated by the bladder is also applied to the prostate (and thus to the BPH) in an additive manner. Pressure generated by the bladder and transferred to the prostate is applied equally to the BPH, so no matter how much pressure is generated by the bladder, and it can be enough to cause the bladder to bulge into pockets between the muscle bundles, it cancels out so the flow of urine is still blocked according to the degree of constriction caused by the amount of BPH present.

BPH in the majority of cases involves the middle lobe of the prostate which cannot be examined through the digital rectal approach. Diagnosis is entirely dependent on the symptoms. There is also no current technology to permit the physician to actually measure the pressure or the volume of BPH present within the prostate.

In addition to BPH, another abnormal condition that may be found within the prostate is the presence of a tumor. The symptoms of BPH are clear and obvious, and the physician can make a general diagnosis on the basis of patient response to questions. Diagnosis of the presence of a tumor, particularly in the early stages, is presently exceedingly difficult to achieve with any degree of reliability. Digital examination through the rectum is used to check the lateral lobes of the prostate for the presence of nodules. If a tumor is large enough, and in an accessible location it can be felt by the examining physician. The middle lobe of the prostate is not accessible via this approach. There is a blood test to detect the presence and amount of a substance called prostate specific antigen, (PSA) which is used to calculate the probability of the presence of cancer within the prostate. However, its use as a screening tool is controversial, and its reliability as a diagnostic tool is not high.

There are Endo-Rectal Ultrasound devices available at this time that can be pressed against the area of the rectum closest to the prostate to provide a means of scanning the prostate to look for signs of cancer. This method also is controversial owing to the difficulty in interpretation of the data. Either digital or endo-rectal ultrasound can be used to guide a biopsy needle to the suspected location. This is a difficult procedure however, as it is done without being able to see where the needle is to be inserted.

During patient evaluation for suspected prostate problems, a cystoscope is usually passed through the urethra into the bladder to assess the general condition of the uro-genital tract. Current cystoscopes are limited to purely visual inspection and add nothing to the physicians' arsenal of tools for the detection of cancer in the absence of an obvious lesion of the urethral wall or a visible mass in the bladder. If a tumor is suspected in any examination a biopsy is made through the rectal wall. None of these procedures have a good track record for accurate diagnosis of the presence of prostate cancer, particularly in the early stages.

If the diagnosis is BPH, there are a limited number of treatments available. In some cases of mild BPH, drug treatment and/or dietary modification may temporarily alleviate the symptoms. Also, there is a treatment for BPH, similar to balloon angioplasty, where the tissue is over-distended mechanically. This, too, is a temporary solution. The best and most common treatment is surgical intervention, generally, the TransUrethral Resection (TUR). In this method, a modified cystoscope, fitted with electrical or mechanical cutters, is introduced into the prostate via the urethra. This device is used to cut away the BPH tissue from the inside of the prostate.

If cancer were to be discovered at an early enough stage, a TUR could be employed to excise that as well. If the tumor is not detected at an early enough stage, treatment will involve the complete removal of the prostate, the lymph nodes of the groin, and possibly, the testicles. The simplest of these procedures involves an operation lasting up to an hour and a half, probably radiation treatment, and secondary complications. The most common secondary complication is the loss of fertility due to retrograde ejaculation. Also, radiation therapy, or mechanical trauma to the muscles can render the sphincters ineffective, thus making the patient incontinent.

The mechanism of retrograde ejaculation is as follows: The urethra, tightly constricted where it passes through the involuntary sphincter, after leaving the bladder opens up with the prostate into roughly a spindle shape. This shape is distorted in the upper region of the prostate by the presence of a longitudinal ridge, called the verumontanum, on one side of the urethra, which makes the urethral opening a "V" shape. This structure is thought to have the function of closing off the pathway to the bladder during ejaculation, thereby forcing the seminal fluid to exit via the penis. The ejaculatory ducts, which bring the sperm into the prostate, empty into the lower portion of the urethra below this area. The glandular tissue that makes up the prostate secretes the necessary seminal fluid to make up the rest of the ejaculate.

A TUR procedure normally destroys the verumontanum structure, permitting the retrograde flow of semen into the bladder. There is little or no semen ejaculated during orgasm, rendering the patient infertile. Although the sensation is said to be the same, the lack of ejaculate may have an adverse psychological effect on some individuals.

In summation; prostate problems are widespread in the older male population. The most common problem is enlarged prostate due to the presence of Benign Prostatic Hyperplasia tissue growth in the middle lobe of the prostate. Prostate cancer is also widespread and much more difficult to diagnose. At present, the best choice for treatment of either BPH or prostate cancer is, which type of surgery will be employed? Dilation and/or drug therapy may be able to temporarily relieve the symptoms but cannot correct the situation. The most popular surgery (TUR) is expensive, with an extended recovery time, no guarantee of permanence, it generally renders the patient infertile, and sometimes incontinent.

There is thus a definite need in the art for an alternate, more effective procedure for detecting, evaluating, and treating BPH and cancer of the prostate. Patents have been granted for "stents" that can be implanted in the prostate to hold open the lumen of the urethra without the necessity for surgery. However, these patented devices serve more in the nature of a stop-gap measure than an effective treatment. None of the patented stents are practically removable should the need arise. None of the patented stents offer any accommodation for variations between individuals. None of the patented "stents" has attempted to take a comprehensive approach to the problem. None of the current approaches enhances the physician's ability to detect, diagnose or quantify the status and progression, or treat abnormalities found in the prostate of a patient.

Accordingly, it is an object of the present invention to provide an accurate, cost effective, system and process for detecting, diagnosing, quantifying the status and progression, as well as treating of any abnormalities found in the prostate of a patient.

It is a further object of the present invention to provide a system for detecting, evaluating and treatment of Benign Prostatic Hyperplasia (BPH) in the prostate of a patient.

A further object of the present invention is a system that serves to provide a dimensional profile of the prostate to permit custom fabrication of a reinforcement insert for a specific patient.

A further object of the present invention is a system that measures the radial pressure within the prostatic urethra and provides the measured pressure in tabular form, relative to the dimensional profile of the prostate, to permit custom design of an implantable reinforcement insert for that individual.

A further object of the present invention is to provide a biocompatible reinforcement insert, custom fitted to the individual, that will maintain the lumen of the prostate open without the necessity for surgical removal of BPH tissue.

A further object of the present invention is an instrument for laying in place a custom made reinforcement insert within the prostatic urethra of an individual and for removal of that reinforcement insert when desired.

Still another object of the present invention is to provide a custom designed reinforcement insert for the prostatic urethra that includes a one way valve, permitting flow of fluid out of the bladder but not back into the bladder.

Still another object of the present invention is to provide a custom designed reinforcement insert for the prostatic urethra that includes a rotary valve that can serve to restore continence to individual patients wherein damage to the sphincter muscles has rendered that patient incontinent.

A further object of the present invention is a system that provides the capability of ultrasonically mapping from within the prostatic urethra the location and volume of any abnormality that may be present.

A further object of the present invention is a system that provides the capability of ultrasonically mapping from within the prostatic urethra, the tissue volume of the prostate at frequencies high enough (up to 50 MHz) to give sufficient resolution to permit diagnosis of malignancy of detected tumors.

Still another object of the present invention is an apparatus and process for providing radioactive treatment to the immediate area of a prostatic cancer, and the removal thereof at expiration of the desired application time.

SUMMARY OF THE INVENTION

According to the present invention the foregoing and additional objects are attained by providing a power driven instrument including a physician controlled, tubular elongated, mapping probe device that is inserted into and advanced through the length of the urethra to the bladder. A transparent, axial pressure sensor, fluid containment element is provided at the tip of the first end of the mapping probe device. The transparent, fluid containment element also serves as the window for a forward-looking fiber optic coupled, video camera. Just behind the tip of the fluid containment element is a second, radial pressure sensor, fluid containment element filling the body of the probe. The second end of the mapping probe devise is secured to a physician controllable, stepper motor driven, gear train, housed within a base structure.

A computer driven display screen is provided in circuit connection with all elements, including; tip and radial pressure transducers; the fiber optic coupled video camera; the ultrasonic tissue scanner; and the stepper motors of the gear train, providing both movement control, and a readout of the position of the probe tip within the urethral tract. In this way, all data is presented on the screen as the mapping probe device traverses the urethral tract, thus providing a complete picture of the conditions within the prostate to the physician for diagnosis.

The base structure includes a miniature video camera and light source coupled to the tip or first end of the fiber optic bundle for conversion and display of the video on the computer driven display.

The base structure also includes a computer which processes all of the data acquired from the various sensors of the mapping probe and converts it into the appropriate on-screen displays.

The base structure computer also provides automatic archiving of all patient data and direct difference comparisons with historical data from the individual patient being evaluated. The permanent data profile provides the following information: A pressure map of, the urethra through the voluntary sphincter; the entrance to the prostatic capsule; the lumen of the prostate; the area of the BPH and/or any tumor (if present); the exit from the prostatic capsule; and, the involuntary sphincter. The data gathered represents radial pressure, or constricting force, and the axial pressure required to push through the two sphincters. The data also includes the exact distances traveled by the probe in order to provide dimensional data. The possession of this information makes it possible to custom fabricate the reinforcement insert element for the individual so that it is configured both to compensate for the sensed pressure patterns, and to fit precisely to lie between the two sphincters and not intrude on their operation.

The data profile also includes a series of circular ultrasonic scans, from within the prostatic urethra, arranged as sequential "slices" perpendicular to the axis of the urethra as it passes through the prostatic capsule. The "slices" taken together permit the imaging of the size, shape, and location of the BPH. They also permit the detection and characterization of any existing tumor in the lateral lobes at a much smaller size than the currently used methods, as well as, in the middle lobe where present methods cannot detect the presence of tumors.

The data profile also contains a video record of the appearance of the interior of the urethra, as well as that of the face of the sphincter areas. This information is valuable in two respects; it permits the physician to evaluate the tone and condition of the sphincters and thus, the possible need to incorporate a controllable anti-incontinence valve into the reinforcement insert, and it also permits the diagnosis of a condition which can exist in some cases where the middle lobe of the prostate has enlarged in the vertical direction so that it protrudes into the floor of the bladder to form a flap of tissue that lies over and occludes the urethral opening. This is a serious condition which can lead rapidly to bladder infection and later to total blockage. The present invention provides for a special reinforcement insert having an extended neck at the upper or first end. The neck extends through the sphincter area with a minimal diameter and then widens slightly to form a wedge shaped protrusion. The protrusion extends just far enough into the bladder to hold the tissue flap from occluding the opening. In such a case, since the involuntary sphincter is rendered inactive, the reinforcement insert is equipped with a controllable anti-incontinence valve to provide substitute action.

The base structure computer also provides access to an online data base oferring comparative data from all patients that have been examined using this system by other physicians. This serves to provide the physician all relevant reference data for his use in making a diagnosis.

When the tip of the mapping probe reaches the bladder, and that area has been inspected optically, the controls are reversed and the mapping probe device withdraws from the patient at essentially the same speed as that employed for insertion thereof.

The pressure, ultrasonic, and visual data are evaluated and, if found needed, a custom designed reinforcement insert is constructed for placement within the prostatic urethra of the patient. The custom designed reinforcement insert is formed of a biocompatible helix of ribbon of suitable metal (such as stainless steel), or plastic (such as one of the polycarbonates, e.g. Lexan), in the shape of a spindle, with the ends thereof being fused to eliminate any sharp edge surfaces. The spindle reinforcement insert provides an enlarged central portion and reduced diameter ends. Other than in the area of the verumontanum, this is the normal shape of the lumen of the prostatic urethra. The reduced end diameter has the effect of producing minimal radial stress counteracting the action of the sphincters, thus minimizing the possibility of secondary incontinence being caused by the presence of the reinforcement insert. A second virtue of the spindle shape is that, since it is accurately sized by the system to the configuration of the individual prostate, it tends to be well located and retained within the prostate.

Yet another virtue of the spindle shape is that the reduced diameter of the ends ensures that the engagement of a removal device is a simple and reliable procedure.

The use of the helical ribbon of biocompatible material for the body of the reinforcement insert provides three major virtues: The relatively broad area of contact with the urethral wall minimizes the possibility of tissue irritation and/or abrasion; the open area between the coils, as well as the rounded cross section of the ribbon material, permit the flow of secretions around and between the coils; and the coil shape permits some lateral flexibility, thus permitting the reinforcement insert to flex slightly, to follow any natural curvature of the urethra, while still resisting any purely compressive forces.

A one-way valve is selectively mounted within the body of the reinforcement insert, at the end disposed towards the bladder, to prevent retrograde ejaculation.

A controllable rotary valve is selectively mounted within the body of the reinforcement insert "downstream" of the location of the one way valve to prevent incontinence if this condition exists or occurs.

Also, suitable radiation treatment pellets may be selectively retained in the desired area of the reinforcement insert to be disposed adjacent to, and for treatment of, specifically located tumors within the prostate.

After the custom reinforcement insert is fabricated to the requirements of the individual patient, the mapping probe element is removed from the gear train of the base structure and replaced by a placement and retrieval probe. The placement and retrieval probe is provided with a lumen through which a placement ram passes to place the reinforcement insert within the prostate or a removal device passes to engage and retrieve the reinforcement insert from the prostate. A fiber optic video pickup is provided within the placement and retrieval probe to monitor these actions.

Both types of probes provide the capability of exuding a topical lubricating and/or anesthetic gel from the tip and through pores spaced along the outside length of the probe for maximum patient comfort.

BRIEF DESCRIPTION OF THE DRAWINGS

A more complete appreciation of the invention and many of the attendant advantages thereof will be better understood when considered in connection with the accompanying drawings wherein:

FIG. 4 is a schematic view illustrating the reinforcement insert of the present invention disposed within the prostatic urethra to treat the problems of the diseased prostate shown in FIG. 3;

FIG. 5 is a schematic illustration of the power drive assembly for both the mapping probe element and the placement and retrieval probe element, and the computer driven display and controls therefor, according to the present invention;

FIGS. 5a, 5b and 5c are schematic illustrations of the various movements of the power driven components during placement and retrieval probe insertion, reinforcement insert placement, and probe withdrawal;

FIG. 9 is a sectional view taken along line IX—IX of FIG. 8;

FIG. 10 is a part schematic, part sectional, view of the mapping probe body and the components thereof;

FIG. 10a is a sectional view of the probe shown in FIG. 10 as seen along line a—a thereof;

FIG. 10b is a sectional view of the probe shown in FIG. 10 as seen along line b—b thereof;

FIG. 12 is a view of the external tip end of the mapping probe shown in FIG. 10;

FIG. 13 is a part schematic, part sectional, view of the diseased prostate having the mapping probe of FIG. 10 disposed therein;

FIG. 14 is a schematic representation of a screen display of one of the ultrasonic "slices" being obtained by the mapping probe shown in FIG. 12;

FIG. 25b is a part perspective view of the engagement mechanism shown in FIGS. 25 and 25a;

DETAILED DESCRIPTION

Figure 1:
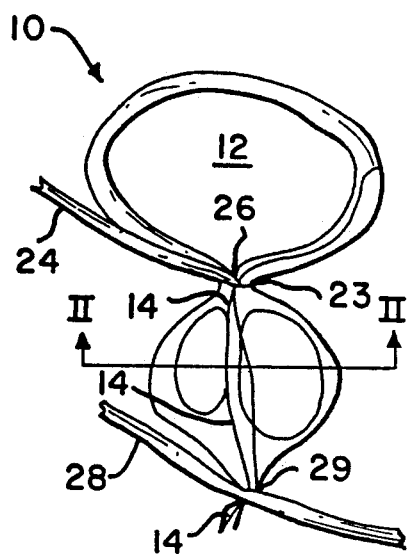
FIG. 1 is a schematic, part sectional, anatomical view of a healthy prostate and adjacent areas of a human male.
Figure 2:
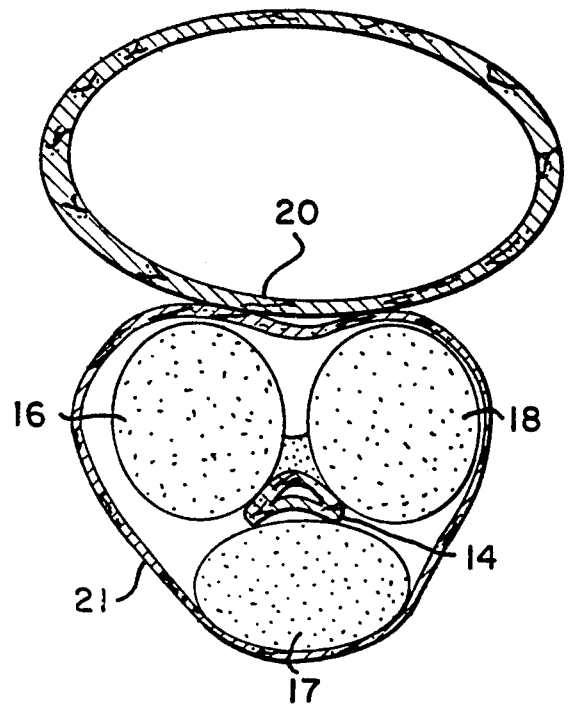
FIG. 2 is a schematic sectional view of the prostate as seen along line II—II of FIG. 1.

Referring now to the drawings, and more particularly to FIGS. 1 and 2, a healthy prostate, generally designated by reference numeral 10, is shown. Prostate 10 is formed of highly glandular tissue and surrounds the urethra 14 just below the urinary bladder 12. In cross section (FIG. 2), prostate 10 shows a triangular arrangement with two prominent lateral lobes 16, 18 lying on either side of urethra 14 on the side closest to the rectal wall 20, and a middle lobe 17. The entire prostate 10 is encased in a tough, relatively thick muscular sheath, or prostatic capsule 21, and attached via a short neck 23 to the base of bladder 12.

Neck 23 passes through a sheet of muscle 24 underlying the fascia covering the bottom of the abdominal cavity. The area of muscle sheet 24 surrounding neck 23 functions as the involuntary sphincter 26 for urethra 14. Involuntary sphincter 26 constricts urethra 14 and prevents leakage of urine volumes too low to be noticeable by the individual, and during sleep, and serves as the primary mechanism responsible for continence. Muscle sheet 28 is disposed beneath prostate 10 and is provided with a constricted opening therein functioning as the voluntary sphincter 29 for urethra 14. The voluntary sphincter 29 is normally closed, and can be voluntarily tightened further, to cope with a distended bladder which would otherwise leak through the sphincters. Urination is effected by relaxation of both sphincters 26 and 29, coupled with muscular contraction of bladder 12 and aided by gravity.

Figure 3:
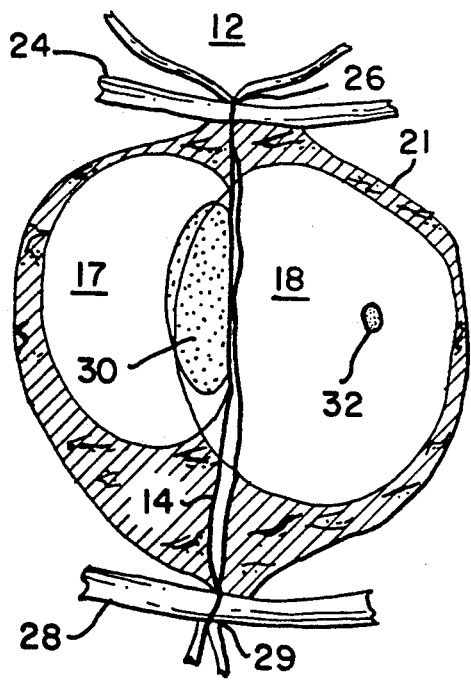
FIG. 3 is a view similar to FIG. 1 and illustrating a diseased prostate.

Referring now more particularly to FIG. 3, a different view of prostate 10 is schematically shown wherein the patient is suffering from Benign Prostatic Hyperplasia (BPH) of middle lobe 17, as designated by reference numeral 30. BPH 30 is a condition where a group of cells, within the prostate, start to grow abnormally. Since the sheath of prostatic capsule 21 is more resistant to deformation than the urethra 14, growth of BPH (which usually occurs in the vicinity of the urethra) pushes inwards preferentially, against the wall of the urethra 14 thus applying pressure that constricts the lumen of the urethra. This constriction obstructs the normal flow of urine, potentially to the point of complete blockage. In this situation, muscle contraction of the bladder cannot overcome the constriction to force the urine through and, emergency action must be taken.

Another abnormal condition that may be found in the prostate is the presence of a tumor, as schematically shown and designated by reference numeral 32. The etiology and structure of BPH and tumors are generally different. BPH generally lies against or surrounds the urethra closely, with a boundary disposed between the BPH and the normal prostatic tissue, and can generally be diagnosed on the basis of patient responses to questions. BPH of the lateral lobes 16, 18 can normally be felt by the physician during a digital examination via the rectum as an enlarged prostate. If BPH is present in the middle lobe 17, it is not available via the digital-rectal approach. Also, there is no current technology that permits actual measurement of the pressure or the volume of BPH present within a prostate.

The diagnosis of a tumor is highly dependent on the size and location of the tumor. If the tumor is located in one of the lateral lobes 16 or 18, and is large enough, it forms a nodule that can be palpated by the physician during a digital-rectal examination. There is also a blood test for the presence of Prostate Specific Antigen (PSA) that is sometimes used during screening to assign a probability factor to the possible presence of a tumor within the prostate. It is however, neither reliable nor qualitative. There are also Endo-Rectal ultrasound devices that can be pressed against the area of the prostate through the rectum but they, also, have not given reliable results. In either case, a biopsy is needed to diagnose a malignancy. This is a difficult procedure because the only access is through the rectum and the area of insertion is blocked by either the digit or the endo-rectal probe. Thus, early detection of prostate cancer with the existing methods is very problematic.

The best current treatment for BPH is the TransUrethral Resection (TUR) in which a modified cystoscope is used to introduce a cutting and cauterizing instrument into the prostate, through the urethra, where it is employed to cut away BPH tissue to relieve the pressure on the urethra. During a TUR procedure, the actual urethra in the area of the BPH is removed, including the area of the verumontanum, which is the inverted "V" shaped protrusion into the urethra illustrated in FIG. 2. It is the loss of this structure that is thought to lead to retrograde ejaculation, the condition where the seminal fluid flows into bladder 12 instead of out through the penis, during orgasm.

Referring more particularly to FIG. 4, a custom made reinforcement insert 35 is shown disposed within urethra 14 to relieve the pressure thereon caused by BPH 30. Reinforcement insert 35 is custom made from pressure data, and other measurements made according to the present invention, as will be further explained hereinafter. The presence of the reinforcement insert 35 also prevents the verumontanum from closing off the urethra during ejaculation which could also lead to retrograde ejaculation. However, reinforcement insert 35 may be fitted with a one-way valve 36, the details of which will be further described hereinafter, that permits fluid flow out of, but not back into, bladder 12. If incontinence is present, reinforcement insert 35 may also be fitted with a controllable rotary valve 120 (FIG. 19) to prevent its occurrence, as will be further explained hereinafter. Suitable radiation pellets 37 may also be carried by reinforcement insert 35 for treatment of tumor 32, as will also be further explained hereinafter.

Referring now more particularly to FIGS. 5, 5a, 5b and 5c, the computerized gear train system for inserting and withdrawing mapping probe 60 and the placement and retrieval probe 110, together with the associated structure thereof, is shown and designated generally by reference numeral 45. Computerized system 45 includes a computer and controls therefor, as designated by reference numeral 47, a display screen 48 and a data recording system 49. Computer and controls 47 are electrically connected to actuate stepper motors 46, 52 and 53. Stepper motor 52 operates to control movement of secondary movement carriage 55 along main movement track 54. Stepper motor 53 controls movement of housing 50 along the track of secondary movement carriage 55. A connector element 57 is disposed on the front of housing 50 to releasably retain either of mapping probe 60 or placement and retrieval probe 110 thereon.

Placement and retrieval probe 110 is inserted through the penis into prostate 10 under the control of a physician through computerized control of stepper motor 52, according to measurements previously made by the mapping probe 60. It moves from the rest position shown in FIG. 5a to approximately that shown in FIG. 5b, as appropriate for the individual patient. A ram 65 is removably attached to the mount 44 at the aft end of secondary movement carriage 55. Ram 65 is slidably received through housing 50, as shown in FIG. 5c, so that when housing 50 moves from the position shown in FIG. 5b under the control of stepper motor 53 to the position shown in FIG. 5c, the tip of the placement and retrieval probe 110 will move back that same distance, but ram 65 will not.

Figure 17:
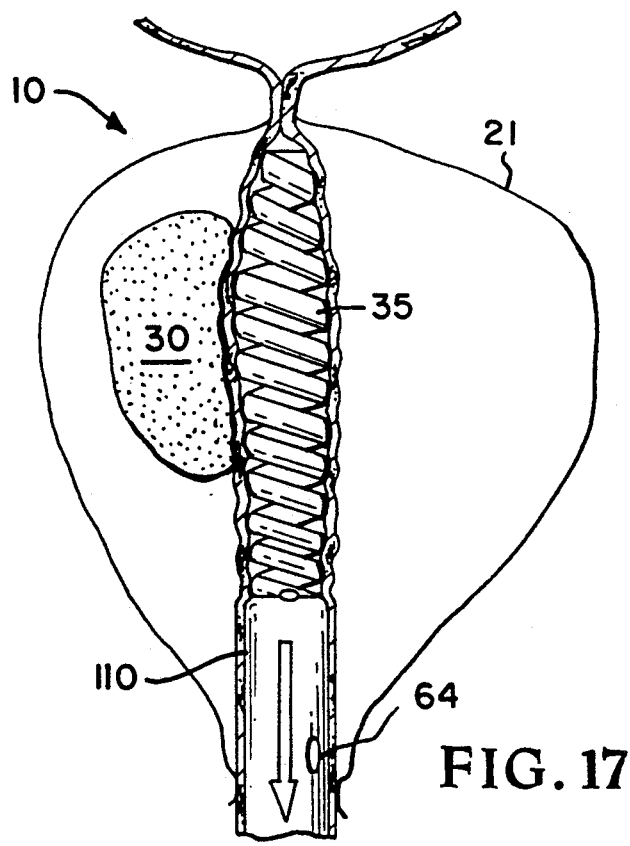
FIG. 17 is a view similar to FIG. 15 illustrating placement of the prostate reinforcement insert and showing further withdrawal of the placement and retrieval probe tube therefrom.

Since the reinforcement insert 35 was previously compressed and placed within the lumen adjacent to the tip of the placement and retrieval probe 110, the effect of the effective contrary movement of ram 65 and the tip of placement and retrieval probe 110 is to push the reinforcement insert 35 out into place within the prostatic urethra. As it emerges, the compressed reinforcement insert 35 will expand to its normal size, pushing out the walls of the urethra, and thus the BPH, to restore free passage for the urine. The pressure of the BPH, together with the locating action of the sphincters at either end, serve to hold reinforcement insert 35 in place, as shown in FIG. 17.

A lubricant and/or anesthesia reservoir 61, supported by housing 50, supplies lubricant and/or an anesthesia gel to either probe via tube 62. The contents of reservoir 61 can be a conventional water soluble medical lubricant gel, a conventional topical anesthesia gel, or a mixture of the two. Each probe is provided with three spaced pores 64 along the length thereof. The mapping probe 60 (FIG. 10) has a circumferential depression 64a around the optical/pressure window at the tip. The placement and retrieval probe 110 delivers the gel, through opening 111, into the terminal portion of the lumen 107 (FIG. 15) near the tip. Lubricant and/or anesthesia gel is dispensed through these ports under pressure as the probe is moved through the urethra to provide maximum patient comfort. In the case of the mapping probe 60, the gel also acts as an acoustic couplant to insure coupling of the ultrasound scanning beam into the tissue of the prostate, as will be further described hereinafter.

Figure 7:
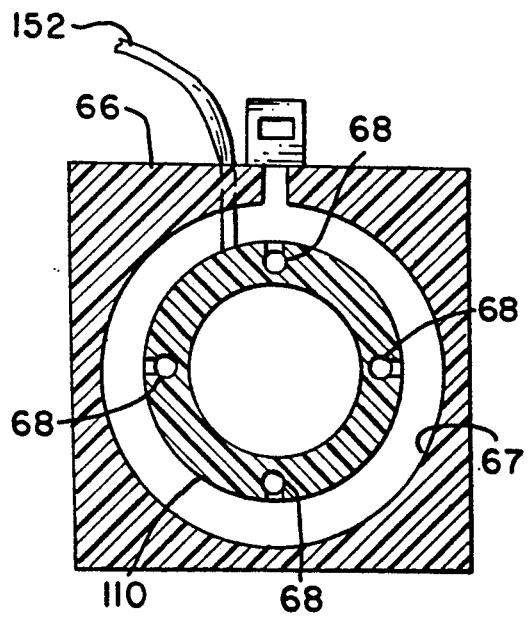
FIG. 7 is a sectional view of the probe lubrication and/or anesthetic passages as seen along line VII—VII of FIG. 6.
Figure 6:
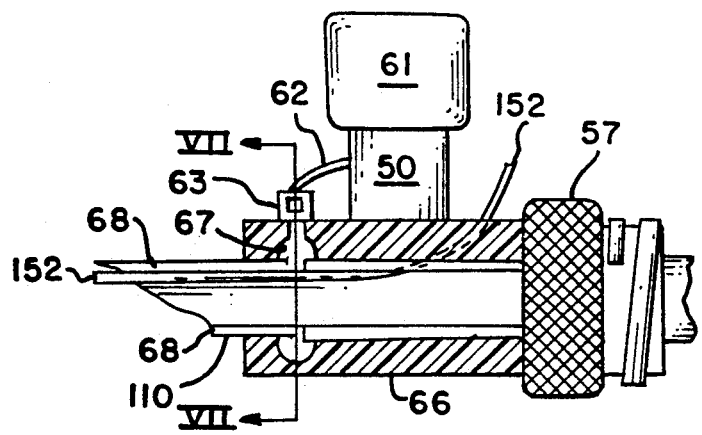
FIG. 6 is a schematic, part sectional, view of the lubricant and/or anesthetic supply and distribution system for the probes of the present invention.

As shown more clearly in FIGS. 6 and 7, lubricant and/or anesthesia gel from reservoir 61 is dispensed through annular chamber 67 into individual tubular passageways 68, each feeding one port 64 or depression 64a. Tubular passageways 68 are equally spaced around the circumference of each of the probes 60 and 110. Probe base 66 is releasably connected to housing 50 via a conventional twist lock assembly 57.

The placement and retrieval probe 110 also incorporates a thin optic fiber 152 extending the length of probe 110 and terminating in a lighted optical lens (FIG. 15), to permit optical verification of the correct placement or removal of reinforcement insert 35.

Figure 8:
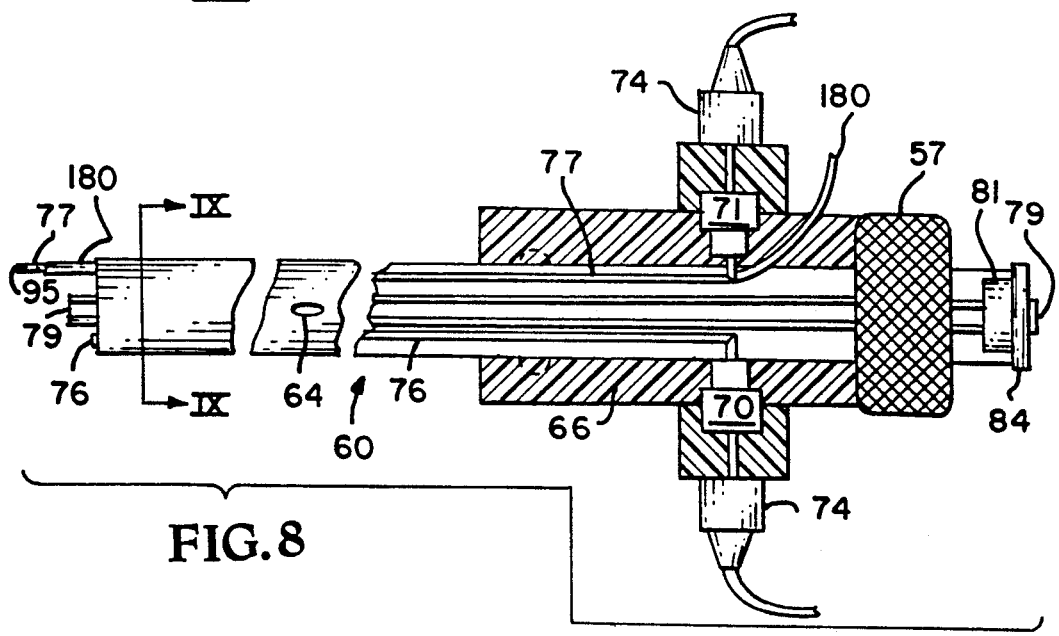
FIG. 8 is a schematic, part sectional, view of the mapping probe base showing the pressure sensor transducers and connection structure therefor.

Referring now more particularly to FIGS. 8 and 9, the pressure sensing components for mapping probe 60 includes a pair of pressure transducers 70, 71 disposed on opposite sides of probe base 66. Suitable respective electrical connectors 73,74 lead from pressure transducers 70,71 to base structure computer 47 where the signals are processed for display on screen 48 (FIG. 5). The pressure transducers 70,71 are located in probe base 66 just aft of the lubrication and/or anesthesia reservoir 61 described hereinabove in reference to FIGS. 6 and 7. A pair of diametrically disposed pressure tubes 76,77 extend from respective pressure transducers 70,71 along the length of the wall of probe 60, as will be further explained hereinafter.

Referring now more particularly to FIG. 10, 10a and 10b, the details of the diagnostic mapping probe 60 will now be described. The lubrication and/or anesthesia gel system details described hereinabove in reference to FIGS. 6 and 7 is omitted in these FIGS. in the interest of clarity.

As shown therein, mapping probe 60 is provided with a hollow drive shaft 79 extending at each end through respective bearings 81,82. Bearing 81 is disposed within mapping probe 60 adjacent to a drive gear 84. One end of drive shaft 79 extends through drive gear 84 to provide egress for the electrical connection to base structure computer 47 (FIG. 5). The other end of hollow drive shaft 79 extends through bearing 82 and is fixed to an end of ultrasonic scanning transducer 88 contained within a transducer housing 89. Transducer housing 89 is disposed within fluid filled chamber 92 just aft of the tip end of mapping probe 60. Fluid 93 in chamber 92 acts as a conductive medium for the propagation of the ultrasound beam, as well as a hydraulic fluid for the pressure sensors. Water is the fluid of choice for fluid 93.

An air backed acoustic mirror 90 is also contained within transducer housing 89 and is disposed at a forty-five degree angle facing, and in spaced relationship with, ultrasonic transducer 88. The forward end of transducer housing 89 is secured to a bearing 83 rotatably disposed within a cavity (not designated) at the end of fluid filled chamber 92. A micro-actuator 91 is provided within transducer housing 89 and is attached to acoustic mirror 90. Micro-actuator 91 controls the curvature of the acoustic mirror to permit a degree of focusing of the ultrasound beam at various depths within the body of the prostate for the purpose of improving the resolution when a suspicious area is detected.

To accomplish this function, micro-actuator 91 is disposed in such a way that it engages the back of acoustic mirror 90. The acoustic mirror 90 takes the form of a very thin-walled box filled with air. When the micro-actuator 91 pulls on the back of the box, deforming it, the volume change within the box lowers the internal pressure. In turn, that will cause fluid 93 in chamber 92 to push the front face of the acoustic mirror box (which it is in direct contact with) to assume a concave shape to equalize the pressures. That, in turn, presents a curved surface upon which the ultrasonic beam impinges giving a focusing effect. The degree of curvature, thus the degree of focus, is directly proportional to the movement of micro-actuator 91. Pressure variations within the chamber 92, related to the radial pressure, are compensated for, if necessary, by the base structure computer controller.

Nose portion 90 of mapping probe 60 is provided with an additional cavity 94 that supports a transparent fluid filled chamber 95. Elongated, fluid filled, tubular pressure conduit 77 extends from pressure transducer 71 and is in fluid connection with fluid filled chamber 95 closed by transparent plastic cover 96. A second tubular fluid filled pressure conduit 76 extends through the body of probe 60 from pressure transducer 70 to provide fluid connection therewith to the fluid filled chamber 92 housing ultrasonic transducer assembly 89.

The transparent fluid filled chamber 95 acts as an axial pressure sensor with the pressure sensed being conveyed through conduit 77 to pressure transducer 71. The measured pressure is processed by base structure computer 47 and displayed on screen 48. The transparent fluid filled chamber 95 also houses and serves as a window for the tip 179 of the fiber optic video system pickup. The thin optical fiber bundle 180 is routed back through the body of probe 60 to connect with a video pickup housed in the base structure where the data is converted for base structure computer 47 to display on screen 48. The fluid filled chamber 92 fills most of the diameter of probe 60 and acts as a radial pressure sensor with the pressure sensed being conveyed through conduit 76 to pressure transducer 70.

Figure 11:
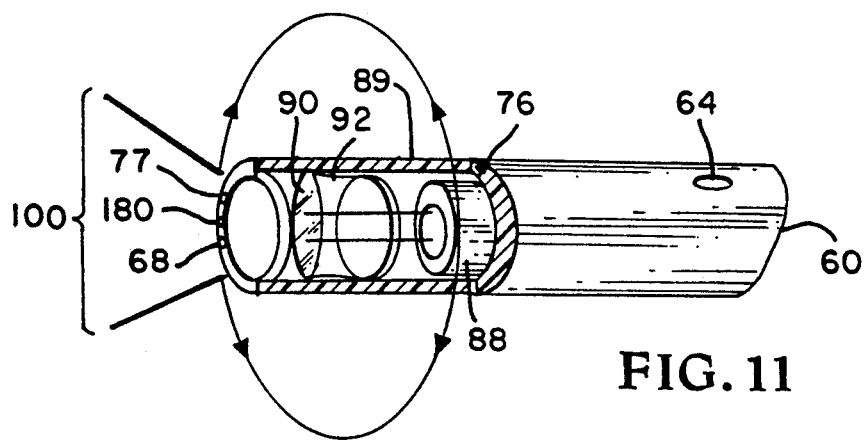
FIG. 11 is an enlarged schematic, part sectional, view of components of the mapping probe shown in FIG. 10.

Referring now to FIGS. 11 and 12, mapping probe 60 is also employed to acquire ultrasonic scans of the prostate tissue as the probe 60 is moved along urethra 14. An ultrasound beam is transmitted by ultrasonic transducer 88, against acoustic mirror 90, which is spaced far enough away to be removed from the beam aberrations of the near field (this is not explained further herein, in the interest of brevity, as it is a concept that is well understood by those skilled in the art). The ultrasonic beam is directed by mirror 90 at right angles to the axis of the probe. The ultrasound beam propagates through fluid 93 which fills chamber 92, through the plastic wall of probe 60 and into the tissue of the prostate as indicated by arrow 98.

The ultrasound system employed is of the "pulse-echo" type, which is well understood by those skilled in the art. It differs from other medical ultrasound scanners by operating at a higher frequency (up to 50 MHz), permitted because of the relatively short depth of penetration required to image what is essentially the radius of the prostate, and by using a variably curved acoustic mirror 90 as a focusing device. The ultrasound beam is reflected back to mirror 90, and from there back to transducer 88 from any structure encountered (i.e. prostate outer wall, tumor, boundary of BPH). The signals are processed by an ultrasonic data acquisition system which is a sub unit of the base structure computer 47, and the resultant data is displayed on screen 48 for the physician's inspection.

As shown in FIG. 12, the exterior surface of mapping probe 60 is provided with two circumferential, and at least one longitudinal, depressed, crease in the outer wall thereof, as designated respectively by reference numerals 102 and 103. This section of mapping probe 60, designated by bracket 104, forms the external surface associated with fluid filled chamber 92. The creases 102 and 103 permit this area to act as a deflectable diaphragm. Pressure supplied by the prostate tissue surrounding this area of probe 60 will deflect the diaphragm proportionately. The deflection of the diaphragm produces a varying hydraulic pressure on fluid 93 contained therein. The varying pressure is passed through conduit 76 to pressure transducer 70. The measured pressure is processed by base structure computer 47 and displayed on screen 48.

By recording the continuous radial pressures exerted on this area of probe 60 as it moves along the urethra, an accurate pressure map of the urethra 14 and prostate 10 is obtained, viewed on display screen 48 and archived by recorder 49.

In order to provide a complete ultrascan scan of the prostate, the ultrasonic transducer housing 89 oscillates within fluid filled chamber 92 over a 340 degree arc of a circle, as probe 60 is stepped through the length of the prostate. The other twenty degrees represents the area through which pass fluid conduit 77 and optical fiber bundle 180, both of which connect to fluid filled chamber 95. Also, through this area passes the lubricant tube 68 connecting with depression 64a. This twenty degree area is directly adjacent to longitudinal crease 103 and designated by bracket 100 in FIG. 11.

One nearly circular slice of prostatic tissue, a few millimeters thick, is scanned at each step and the data is processed and displayed on screen 48. When the probe tip has reached the end of the prostatic capsule 21 (the involuntary sphincter 26), the body of probe 60 is rotated twenty-five degrees on its axis and the direction of movement is reversed. This action brings into the field of view of the ultrasonic scanner that area which was not scanned during the inward movement of the probe. Ultrasonic scanning then continues as the probe tip steps back through prostatic capsule 21. On completion of the scanning of prostatic capsule 21, the entire probe 60 is withdrawn from the patient.

Referring now to FIG. 13, mapping pressure probe 60 is shown as it is being inserted through urethra 14 of a diseased prostate 10. As shown therein, the oscillating beam 98, passes through the structures of the prostate tissue, returning a time displaced echo from each structure encountered. These structures include the first surface of BPH mass 30; the second surface of BPH mass 30; the first surface of tumor 32; the second surface of tumor 32; and finally, the outer wall 21 of the prostate. Additionally, the variations in density between the different structures will modulate the beam strength in such a manner as to permit type characterization of those structures to facilitate diagnosis by the physician.

Referring now to FIG. 14, a schematic example is shown of the screen display 48, depicting what would result from a step scan made at the point shown in FIG. 13. As shown therein, the outline and texture of BPH mass 30; the outline and texture of tumor 32; and the outline of the prostatic capsule 21, can all be seen. The shadow of the unscanned twenty degree segment lies on the bottom radial of this scan, which is addressed in the return scan. The numerical pressure readings are simultaneously shown on display screen 48, but are not shown in this Figure for clarity.

The numerical pressure readings, and the pictorial display appearing on screen 48 (FIG. 14), are simultaneously being recorded by recorder 49 to form a complete and permanent record profile of the area scanned by mapping probe 60. In addition to pressure measurements and ultrasonic tissue characterization scans, mapping probe 60 provides a linear measurement of geometrical relationships between all features along the length of the urethra.

Water, or other suitable transparent hydraulic fluid 93, fills chamber 92 where it acts (1) to transfer hydraulic pressure, resulting from radial compression of the urethral wall (and thus any BPH present), to pressure transducer 70 in probe base 66, and (2) to serve as a propagation medium for the ultrasound scanning beam 98. Water, or other suitable transparent hydraulic fluid 93, also fills chamber 95 where it acts to (1) transfer hydraulic pressure resulting from axial pressure when the probe tip encounters the two (initially closed) sphincters, and (2) to serve as an optical medium, for the optical fiber videoscope. The transparent plastic covering 96 of chamber 95 serves as a window for the optical system.

Figure 15:
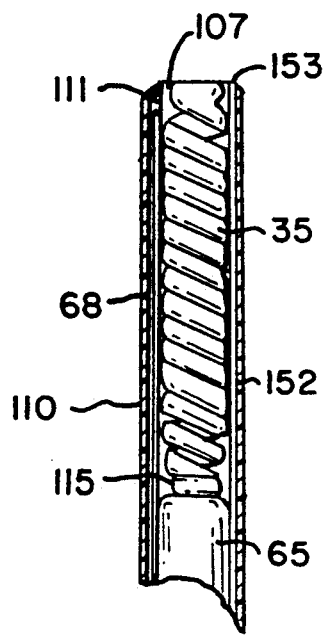
FIG. 15 is a schematic, part sectional, view of the prostate reinforcement insert of the present invention within the lumen of the placement and retrieval probe and adjacent to the placement ram therein.

Referring now to FIG. 15, a part sectional, schematic view of a reinforcement insert 35 is shown. Reinforcement insert 35 is custom fabricated utilizing the pressure and linear measurement data obtained from mapping probe 60, and is employed to alleviate the diseased conditions diagnosed from the mapping probe 60 data obtained, as described hereinabove. Reinforcement insert 35, as described hereinbefore, is formed of a biocompatible plastic or metal helix of ribbon and is spindle shaped.

For placement, reinforcement insert 35 is compressed within the lumen 107 of one end of placement and retrieval probe tube 110. One end of reinforcement insert 35 is disposed against a first end of ram 65 that is slidably disposed within placement and retrieval probe 110. An optical fiber 152 is disposed within the wall of the placement and retrieval probe tube 110. Optical fiber 152 is in communication with the video system (not shown in this Figure but described hereinbefore) for display on screen 48. Placement and retrieval probe 110 is equipped with the lubricant and/or anesthesia dispensing system as described hereinbefore in reference to FIGS. 5-7.

Placement and retrieval probe tube 110 is secured to housing 50 via twist lock 57 in the same manner as described hereinbefore for mapping probe 60. Ram 65 slidably extends through housing 50 with one end thereof attached to mount 44 at the aft end of secondary movement carriage 55 via a clamp type lock (not illustrated). In this manner, ram 65 is stationary relative to placement and retrieval probe tube 110 and housing 50, which are slidably activated by the secondary movement 55 under the control of stepper motor 53. The other end of ram 65 extends into placement and retrieval probe 110 to engage end 115 of reinforcement insert 35 after it has been compressed into the end of lumen 107 of the probe 110, as shown in FIG. 15.

Referring now back to FIGS. 5a-5c, housing 50 is shown at the forward end of the secondary movement track 55, which is in turn, at the aft end of the main movement 54 (FIG. 5a). In FIG. 5b, the end of placement and retrieval probe 110 is inserted into the urethra. Under the physician's control, through computer 47, the secondary movement carriage 55 is advanced along the main movement 54 by stepper motor 52, through urethra 14 into the prostate, until the probe tip lies directly adjacent to involuntary sphincter 26.

As shown in FIG. 5c, when the tip of placement and retrieval probe 110 is in the correct location, housing 50 which carries probe tube 110, moves backwards on the secondary movement track 55 a distance equal to the length of the reinforcement insert 35 to be placed. The ram 65 does not move during this action, thereby keeping the reinforcement insert 35 stationary. This process leaves the reinforcement insert 35 in the proper location within the prostatic urethra, expanding to its normal size as probe tube 110 is withdrawn from around it. Placement is verified by the physician via the optical video display seen by optical fiber pickup 153 and displayed on screen 48.

Figure 16:
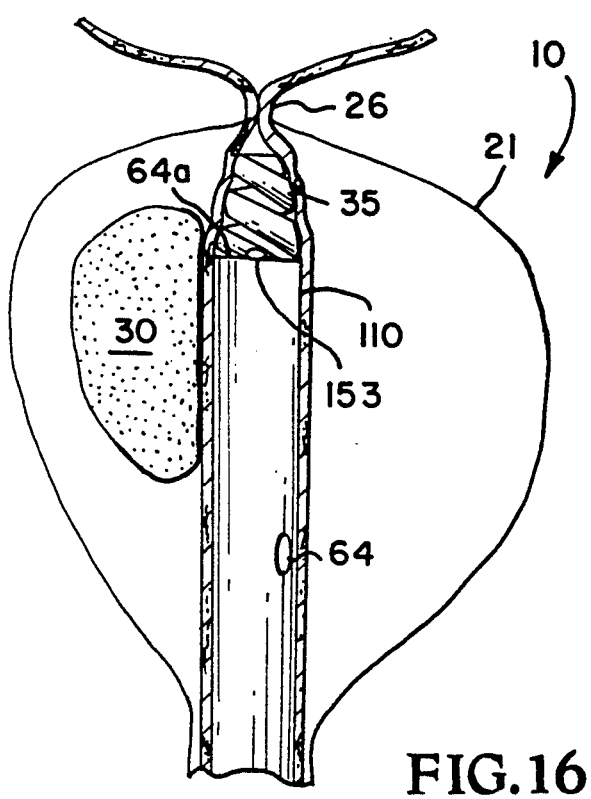
FIG. 16 is a view of the prostate reinforcement insert shown in FIG. 15 when being placed in position within the urethra of a diseased prostate.

Referring now to FIGS. 16 and 17, reinforcement insert 35 is shown beginning to emerge from the lumen of probe 110 in FIG. 16 and almost completely out in FIG. 17. The placement and retrieval probe tube 110, together with ram 65, are then withdrawn from the patient to complete the "laying in place" of reinforcement insert 35 within urethra 14 and disposed between involuntary sphincter 26 and voluntary sphincter 29 (except for a modified case involving an occluding flap, as will be described hereinafter).

Figure 18:
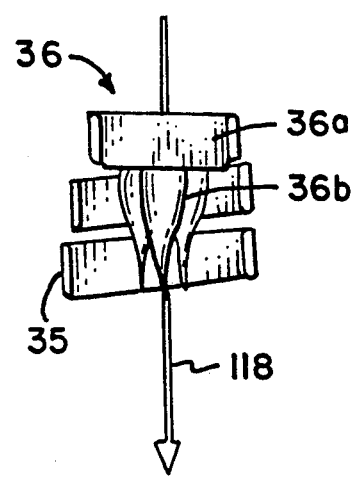
FIG. 18 is a schematic, part sectional, view of the one-way valve shown in FIG. 4 in the open position.

As discussed hereinbefore, in reference to FIG. 4, and as also shown in FIG. 18, a one-way valve 36 may be secured within reinforcement insert 35 and disposed within the end thereof adjacent involuntary sphincter 26 to prevent retrograde ejaculation. One-way valve 36 is shown in open position in FIG. 18 and includes an annular ring 36a bonded or otherwise fixedly secured within the end of reinforcement insert 35.

Annular ring 36a, bears a plurality of conical shaped depending petals 36b. Petals 36b overlap each other and are normally resiliently maintained in the closed position shown in FIG. 4 to prevent retrograde flow from prostate 10 into bladder 12. Flow from bladder 12 into urethra 14 within prostate 10 (as depicted by arrow 118 in FIG. 18) is permitted by valve 36 due to the fluid pressure overcoming the resiliency of the petal segments. Once involuntary sphincter 26 is closed, the petals 36b resiliently close and retrograde flow into bladder 12 is again prevented. Ring 36a and petals 36b are formed of Silastic or other suitable biocompatible elastomeric material.

Figure 19:
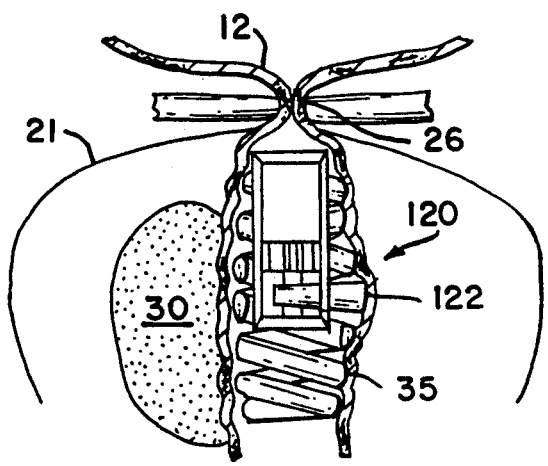
FIG. 19 is a schematic, part sectional, view similar to FIG. 4 and illustrating a controllable rotary valve assembly disposed within the reinforcement insert.
Figure 20:
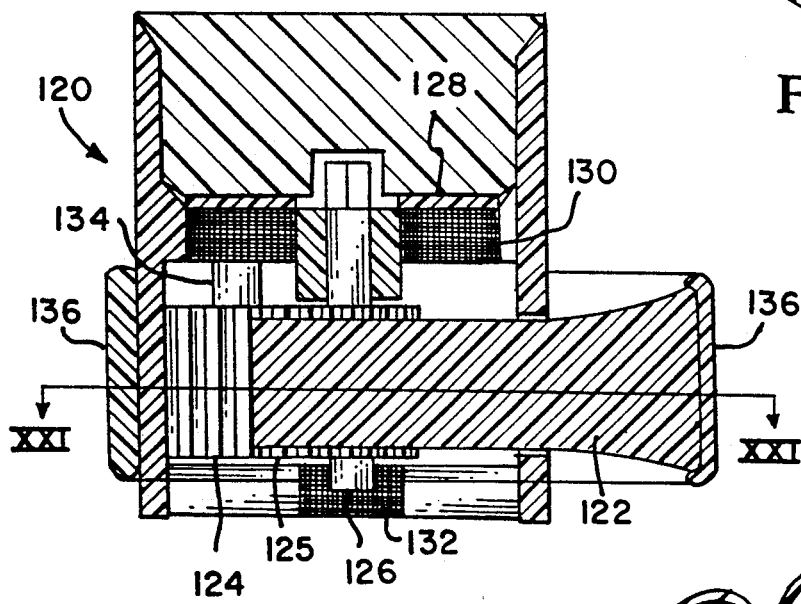
FIG. 20 is an enlarged, part sectional, view of the valve assembly shown in FIG. 19.

Referring now to FIGS. 19 and 20, a controllable rotary valve body 120, which can be fitted into reinforcement insert 35 to alleviate the symptoms of incontinence, is shown. Valve 120 is a rotary valve with rotation of the valve opening and closure element being actuated by a pawl 122. Pawl 122 acts against drive gear 124 to rotate a second gear 125 fixed to a drive shaft 126. Drive shaft 126 is fixed to a perforated rotary valve disc 128. Rotation of rotary valve disc 128 causes the openings therein to align with identical openings provided in a circular web 130. Web 130 is bonded or otherwise secured to the interior wall of valve body 120 to prevent relative rotation therebetween. A fixed elongated drive shaft support web 132 rotatably supports the lower end of drive shaft 126 therein. An axle 134 is fixed to web 130 and rotatably supports drive gear 124 thereon.

Figure 22:
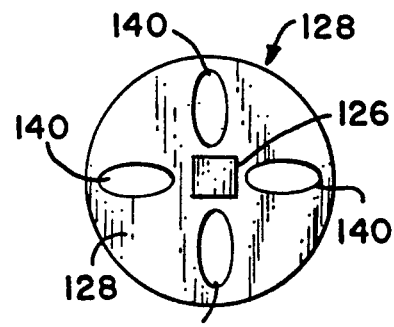
FIG. 22 is a schematic plan view of the rotary valve actuated by the pawl and gear drive shown in FIG. 21.
Figure 23:
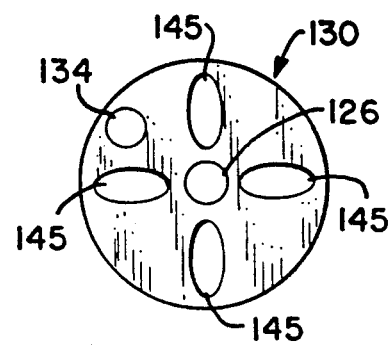
FIG. 23 is a schematic plan view of the stationary web disposed adjacent to the rotary valve of FIG. 22.
Figure 21:
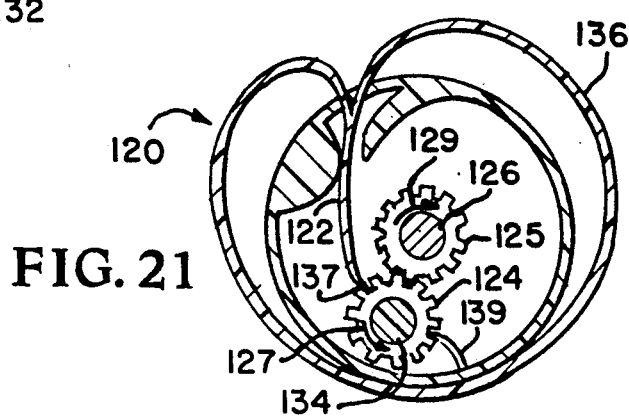
FIG. 21 is a schematic sectional view of the pawl and gear drive actuator for the rotary valve shown in FIGS. 19 and 20, as seen along line XXI—XXI of FIG. 20.

The operation of one-way valve 120 is best understood by reference to FIGS. 21, 22 and 23. As shown therein, the exterior of pawl 122 is essentially in the form of a compression ring 136 having a tip end 137 extending internally thereof. Compression ring 136 protrudes through the body of reinforcement insert 35 and bears against the wall of urethra 14. The tip 137 of pawl 122 angularly engages a space between two teeth on drive gear 124. Inwardly radial pressure on compression ring 136 applied by voluntary contraction of bladder 12, as normally exerted during voluntary urination, collapses the ring, pushing pawl 122 inward, thus moving the tip portion 137 thereof to effect rotation of drive gear 124 in the direction indicated by arrow 127 thereon (FIG. 21). The tensile strength of compression ring 136 is dictated by the differential between the inwardly radial pressure being supplied by the BPH and the excess pressure available from voluntary contraction of the bladder, both of which are measured by mapping probe 60 and made available for fabrication of custom reinforcement insert 35, and rotary valve 120.

A flexible pawl 139 is secured to the inner surface of valve body 120 and also engages drive gear 124 between two teeth thereon to insure that any rotation of drive gear 124 is confined to the one direction. Rotation of drive gear 124 effects rotation of second gear 125 in the opposite direction as indicated by arrow 129. Rotation of second gear 125 also effects rotation of drive shaft 126 and attached rotary valve disc 128.

As shown in FIGS. 22 and 23, rotary valve disc 128 is provided with a plurality of openings therein equally spaced along the periphery thereof, as designated by reference numeral 140. Circular web 130, as described hereinbefore, is fixed to the inside of valve housing 120, and is also provided with a plurality of openings 145. Openings 145 are equal in size, number and relative location on web 130 as openings 140 in rotary valve disc 128. When aligned, openings 140 and 145 permit flow from bladder 12 into urethra 14 for urination. When rotary valve disc 128 is rotated to remove openings 140 therein from alignment with openings 145 in circular web 130, no flow is permitted from bladder 12 to urethra 14.

The contraction of urethra 14 is a secondary effect of voluntary contraction of the bladder by an individual. Each contraction will effect some rotation of rotary valve disc 128 through the action of pawl 122 toward opening of valve 120 to permit normal urination. Additional contractions will cause rotary valve disc 128 to rotate further and move openings 140 out of alignment with openings 145 and thereby close valve 120 to prevent leakage. The number of contractions required for opening and closing the valve assembly may vary between individuals but, through practice, should prove no problem in each individual determining his own operability range thereof.

An alternate embodiment of a rotary valve, for use in those individuals who lack sufficient muscle tone to actuate the compression ring mechanism, would be to eliminate the compression ring and gear train and substitute a ratcheting, ring shaped, piezo-electric actuator. Such a device would operate in the same manner as similar actuators which are used to power auto-focus mechanisms in cameras. They are small, light in weight and could be incorporated at the interface between the edge of the rotating valve and the valve body. Such a device would be actuated by electrical pulses conducted along a very small cable passing up through the urethra and attached to an implanted control element at the base of the penis.

Referring now to FIGS. 24a, 24b, 25, 25a, and 25b, when it is necessary to remove or retrieve reinforcement insert 35 from prostate 10, a capture mechanism 147 is employed. Capture mechanism 147 is a half turn, coarse threaded shaft, mounted concentrically on the face end of removal tool 149. Removal tool 149 takes the form of a modified elongated ram disposed slidably and rotatably within the lumen of placement and retrieval probe 110. Movement of placement and retrieval probe tube 110, as well as the linear and rotative movement of removal mechanism/tool 147/149 is controlled by the physician through stepper motors 52, 53 and 46 on the main and secondary movement assemblies 54 and 55 (FIGS. 5-7).

Figure 24A:
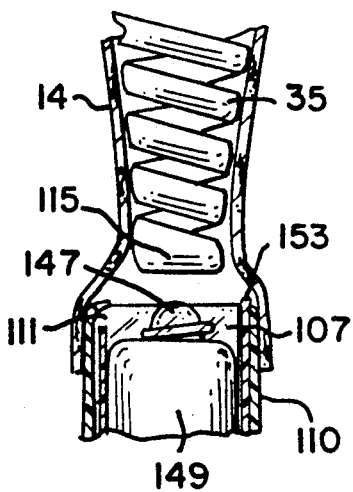
FIGS. 24a and 24b are part plan views of the engagement mechanism, respectively, approaching the reinforcement insert and, being locked in place within the reinforcement insert for retrieval thereof from a prostate.
Figure 24B:
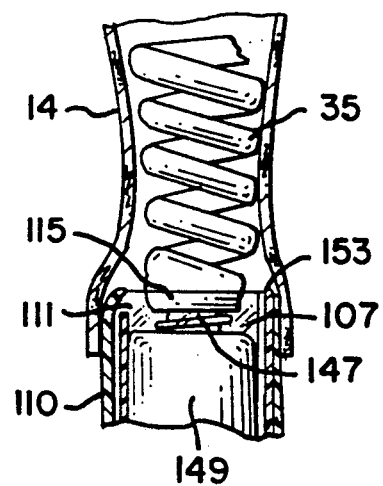

The initial condition of the probe assembly is that housing 50, together with probe 110, is at the aft end of the travel of secondary movement track 55. Removal tool 147/149 is inserted through the lumen of probe 110 so that the tip of removal mechanism 147 is immediately adjacent to the open end of probe 110, as shown in FIG. 24a. At that point, the shaft of removal tool 149 is rotatably secured to the mount 44 at the aft end of secondary movement carriage 55. The tip of probe 110 is inserted into the urethra and advanced through the urethra until it passes through voluntary sphincter 29 and comes in contact with end 115 of reinforcement insert 35, as shown in FIG. 24b. This point is known from the recorded data gathered by mapping probe 60 in the manner described hereinbefore.

Figure 25:
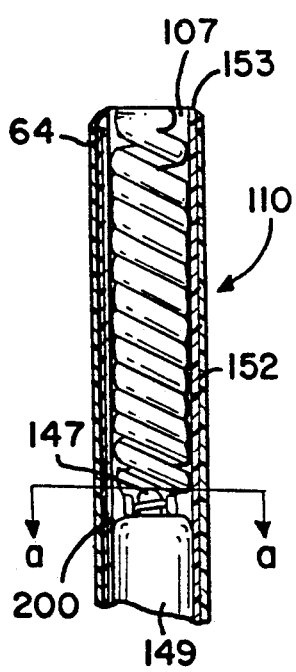
FIG. 25 is a schematic, part sectional, view of the engagement mechanism shown in FIG. 24a and 24b when the reinforcement insert has been recaptured within the lumen of the placement and retrieval probe tube prior to total withdrawal from the patient.
Figure 25A:
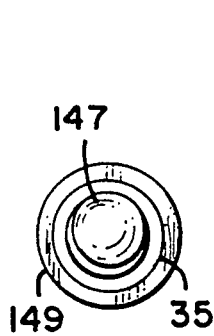
FIG. 25a is a schematic section of the engagement mechanism taken along line a—a of FIG. 25.
Figure 25B:
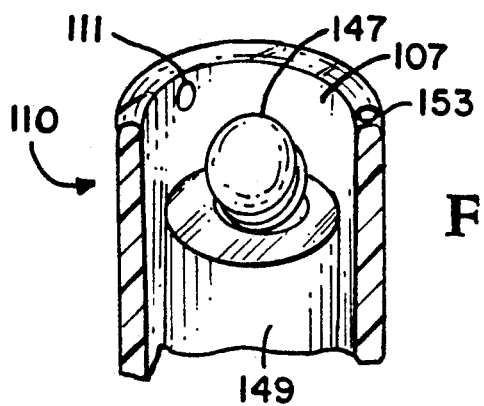

The placement is verified by direct observation by the physician via the optical fiber video display. As shown in FIG. 25, when the capture mechanism 147 is in contact with the end 115 of reinforcement insert 35, it is rotated by stepper motor 46 to engage the threaded capture mechanism 147 into the threaded receptacle 200 within the end of reinforcement insert 35. In the present invention, the end of reinforcement insert 35 is smaller than the lumen of probe 110 making the capture a simple procedure.

As soon as the physician sees the reinforcement insert 35 begin to rotate on the video display 48, secondary movement 55 is activated. This moves housing 50, and thus the end of probe tube 110 forward, while the removal tool 149 (and therefore the reinforcement insert 35) continues to slowly rotate in such a manner that the helix of the reinforcement insert 35 moves into the lumen 107 of probe tube 110 at the same rate that the probe tube 110 is advanced. This action provides minimum friction both to the urethral walls and to the recompression of reinforcement insert 35 back into lumen 107 of placement and retrieval probe tube 110. Main movement assembly 54 is then employed to completely withdraw placement and retrieval probe 110 and its contents from the patient.

Figure 26:
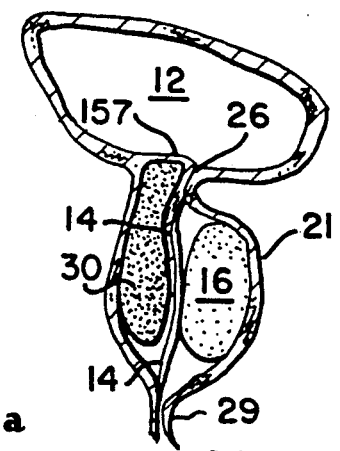
FIG. 26 is a schematic view of an extremely enlarged BPH of the prostate extending against and distorting the bladder to form an occluding flap, closing the urethral exit from the bladder.
Figure 27:
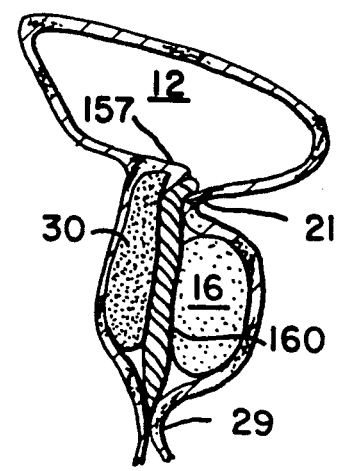
FIG. 27 is a view similar to FIG. 26 illustrating a custom designed reinforcement insert employed to alleviate the problems caused by the condition shown in FIG. 26.

Referring now to FIG. 26, an extremely enlarged BPH 30 of the middle lobe 17 of a prostate 10 is illustrated. As shown therein, BPH 30 has enlarged to such an extent that it engages bladder 12, forcing a portion thereof to form an occludent flap 157 that completely closes involuntary sphincter 26 and prevents any urine flow from bladder 12 into urethra 14. To alleviate this condition, a reinforcement insert 160 is custom made from information obtained via use of mapping probe 60. Reinforcement insert 160 is formed of the same biocompatible plastic (or metal) as that employed in making reinforcement insert 35 but has an extended neck at the upper end which is passed through involuntary sphincter 26 to support the tissue flap 157, preventing it from blocking the opening to the urethra. This type of reinforcement insert will render the involuntary sphincter 26 ineffective thus necessitating the incorporation of the controllable rotary valve 120. Obviously, in this situation, mapping probe 60 must be advanced to a point just within bladder 12 during pressure determinations and mapping of urethra 14.

Figure 28:
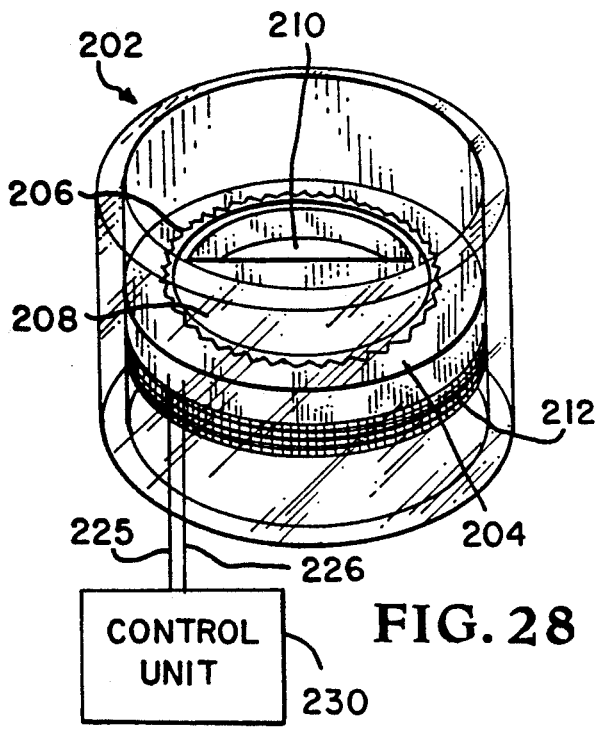
FIG. 28 is a part schematic, part perspective view, with portions cut away, and portions omitted, showing a controllable piezo-electric valve disposed within the reinforcement insert.

Another alternate embodiment of a rotary valve, for use by those individuals who lack sufficient muscle tone to actuate the compression mechanism ring 136, described hereinbefore in reference to rotary valve 120, would be to eliminate the compression ring and gear train arrangement and substitute a ratcheting, ring shaped, piezo-electric actuator, as illustrated in FIGS. 28-30, and designated generally by reference numeral 202.

Piezo-electric valve 202 operates in the same manner as similar actuators presently employed to power auto-focus mechanisms in cameras. These devices are small, light in weight, and could be readily incorporated at the interface between the edge of the rotating valve and the valve body and are mounted within reinforcement insert 35 in the same manner as rotary valve 120, shown in FIG. 19, but differ in internal construction.

As shown in FIG. 28, valve body 202 has a non-rotatable web 212 disposed within the lumen of the valve body 202. Mounted adjacent to, and in contact with, fixed web 212 is a rotatable disc valve 208. The periphery of disc valve 208 is fitted with a circular piezo-electric element 206. Piezo-electric element 206 is toothed on its outer surface to engage matching teeth on the inner surface of piezo-electric element 204. Piezo-electric element 204 is an internally toothed ring, mounted non-rotatably to the inner surface of valve body 202.

Rotatable disc valve 208 is perforated by a single semicircular opening 210 which is slightly smaller that one-half the area of disc 208.

Figure 29A:
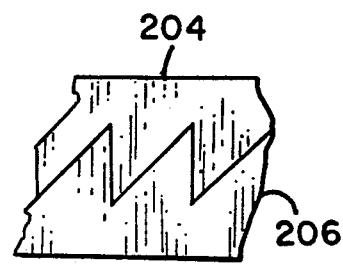
FIGS. 29a, 29b, and 29c are detailed views of a portion of the piezo-electric actuating element showing sequential movement of the piezo-electric parts of the valve shown in FIG. 28.
Figure 29B:
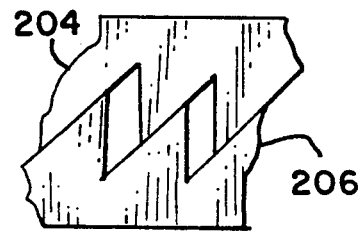
Figure 29C:
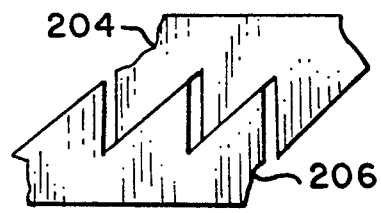

Referring to FIGS. 29a, 29b and 29c, the action of the complimentary piezo-electric elements 204 and 206 is illustrated. The shape of the mating teeth on the respective elements 204 and 206 is that of a right triangle, giving the effect of a relatively sloping ramp with a steep drop at the end. When an electrical pulse is applied to the toothed ring, the shape of the piezo-electric material from which it is made will distort. The proper application of a group of pulses to the mating piezo-electric elements 204 and 206 will cause the teeth of ring 206 to ride up the ramps of the mating teeth of ring 204 (FIG. 29b) until they drop over the crest into the next depression (FIG. 29c). This action represents one step of rotation and takes place each time that electrical pulses are applied to the piezo-electric elements 204 and 206. The piezo-electric valve action is thus similar to that of a stepper motor, with one specifically sized step accomplished at each applied pulse. In this manner, a train of a known number of closely spaced electrical pulses will effect a rotation of ring 206, and thus, the attached rotary disc, over a known and specific number of degrees of rotation.

Figure 30A:
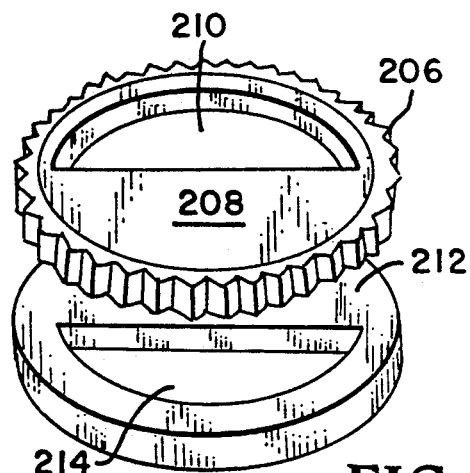
FIGS. 30a, 30b and 30c schematically illustrate the operation of the fixed web and rotary valve portions of the piezo-electric valve shown in FIG. 28.
Figure 30B:
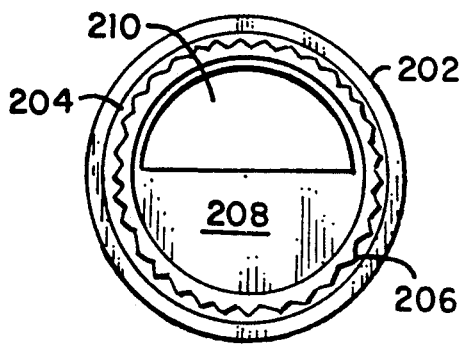
Figure 30C:
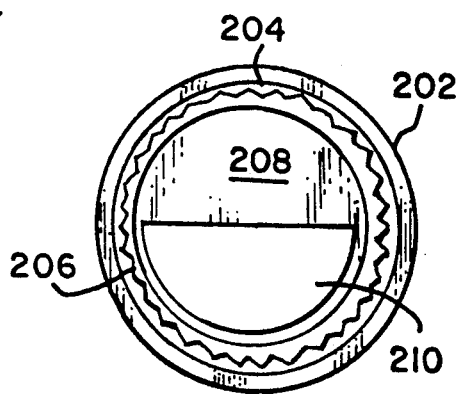

Referring now to FIGS. 30a, 30b and 30c it is seen that the application of a predetermined pulse train by control unit 230 (FIG. 28) will result in the rotation of valve disc 208 by 180 degrees. FIG. 30a shows fixed web 212 having a semi-circular opening 214 therein. Opening 214 is of the same size and configuration as the opening 210 in valve disc 208. Therefore, a 180 degree rotational valve disc 208 alternately aligns the openings, permitting the flow of urine therethrough, or to place the openings 180 degrees out of alignment, to close off the flow of urine, as shown in FIGS. 30b and 30c.

Referring back to FIG. 28, the electric pulses for actuation of piezo-electric valve 202 are carried by two small, teflon coated, wires 225 and 226 which pass through the urethra. Wires 225 and 226 are small enough to not interfere with the flow of urine around them. Wires 225 and 226 terminate in a control unit embedded in the skin at the base of the penis, as schematically shown by box 230. Actuation of valve 202 is thus controlled by placing a suitable hand held activator against the skin, adjacent to control unit 230.

Although the invention has been described relative to specific embodiments thereof, it is not so limited and there are numerous variations and modifications of the invention that will be readily apparent to those skilled in the art in the light of the above teachings. For example, although the invention as described herein has been specifically directed to problems in the male of the species, applications thereof may also be employed to alleviate some urethral problems found in the female of the species.

It is therefore to be understood that, within the scope of the appended claims, the invention may be practiced other than as specifically described herein.

We claim:

1. A system for detecting, evaluating and treatment of prostate and urinary problems in a male human comprising:
   a computerized base structure including a computer and physician operated controls therefor, a display screen and a data recording means;
   said computerized base structure also including a fixed main movement track and a secondary movement carriage linearly movable along said main movement track;
   a probe support housing supported by and movable with said secondary movement carriage, as well as, movable independently, and linearly, relative to said secondary movement carriage;
   computer controlled first motor means for selectively moving said secondary movement linearly along said main movement track;
   computer controlled second motor means for selectively moving said support housing linearly along said secondary carriage;
   an elongated tubular probe;
   a locking assembly carried by said probe support housing for releasably securing said elongated tubular probe thereto and disposed in parallel relationship with said fixed main track on said computerized base structure;
   said elongated tubular probe being dimensioned to be received within the urethra of a male patient and to have the capability of extending from the tip of the penis, through the prostate, and to just within the bladder of the patient; and said elongated tubular probe being selected from the group of elongated tubular probes consisting of a mapping probe and a placement and retrieval probe.

2. The system of claim 1 wherein said elongated tubular probe is a mapping probe, said mapping probe including:
   first and second fluid filled chambers;
   a transparent hydraulic fluid filling each of said first and said second fluid filled chambers;
   said first and said second fluid filled chambers being in hydraulic fluid connection with respective first and second pressure sensing transducers;
   said first and said second pressure sensing transducers sensing axial and radial pressure encountered by said mapping probe and being in connection with said computer, said display screen and said data recording means to display and record a spatial pressure density map of the axial and radial pressures relative to incremental length within the prostatic urethra.

3. The system of claim 2 wherein said transparent hydraulic fluid filling each of said first and said second fluid filled chambers is water.

4. The system of claim 2 wherein said mapping probe has a first unattached tip end and a second end releasably attached to said lock assembly;
   said first hydraulic fluid filled chamber being disposed at said tip end of said mapping probe and including a flexible, transparent, plastic cover housing a quantity of said transparent hydraulic fluid; said flexible, transparent, plastic cover being deflectable by external axial pressure;
   a fiber optic lens disposed within said first hydraulic fluid filled chamber;
   a fiber optic bundle connected to, and extending from said fiber optic lens, through said mapping probe to connect with a video pickup housed within said computerized base structure;
   said fiber optic lens and said fiber optic bundle providing visual indication on said display screen, and a permanent record on said data recording means, of the area encountered by said unattached tip end of said mapping probe as said mapping probe is inserted along the path of the urethra under the control of a physician.

5. The system of claim 4 wherein said second fluid filled chamber is disposed in spaced adjacency to said first fluid filled chamber and aft of said tip end of said mapping probe;

said second fluid filled chamber having a diameter equal to the interior diameter of said mapping probe and in fluid communication with said second pressure sensing transducer;

an ultrasonic transducer housing rotatably disposed within said second fluid filled chamber;

an ultrasonic transducer housed within said ultrasonic transducer housing; and an air backed acoustic mirror also contained within said ultrasonic transducer housing and disposed at a forty-five angle facing, and in spaced relationship with said ultrasonic transducer.

6. The system of claim 5 including, at least the portion of said mapping probe forming said second fluid filled chamber being formed of an acoustically transparent plastic material;

said acoustically transparent plastic material being provided with a circumferential, depressed, crease in the exterior surface thereof at each end of said second fluid filled chamber, and at least one longitudinal depressed crease formed in said acoustically transparent plastic material and extending between said circumferential depressed creases; whereby, said portion of said mapping probe forming said second fluid filled chamber is deflectable by external radial pressure, with any deflection being transmitted by the hydraulic fluid in said second fluid filled chamber to said second pressure transducer, and displayed and recorded, respectively, by said display screen and said data recording means.

7. The system of claim 5 including focusing means for said acoustic mirror;

said focusing means including a micro-actuator engaging the back of said air backed acoustic mirror;

said micro-actuator serving to change the curvature of said air backed acoustic mirror to provide an adjustable focal length for the ultrasonic beam impinging on said mirror in direct proportion to the movement of said micro-actuator.

8. The system of claim 7 including, a reinforcement insert for a diseased prostate;

said reinforcement insert being custom designed from dimensional, optical, axial pressure, radial pressure data and ultrasonic scan data obtained from physician operation of said mapping probe during the examination of the prostate of a patient.

9. The system of claim 1 including lubrication and/or anesthesia dispensing means for said elongated tubular probe;

said lubrication and/or anesthesia dispensing means including a reservoir supported by said support housing and containing a pressurized source of at least one gel selected from the group of gels consisting of lubricant gels and topical anesthesia gel;

an annular chamber disposed about said elongated tubular probe and in spaced adjacency to said locking assembly for releasably securing said elongated tubular probe thereto;

said annular chamber being in fluid communication with said reservoir;

a plurality of tubular passageways in fluid communication with said annular chamber;

said plurality of tubular passageways being disposed in parallel spaced relationship within said elongated tubular probe;

at least one of said plurality of tubular passageways extending the length of said elongated tubular probe and opening adjacent the end thereof opposite to the end thereof releasably secured to said locking assembly; and the remaining of said plurality of tubular passageways terminating individually at spaced exterior ports disposed along the length of said elongated tubular probe.

10. The system of claim 1 wherein said elongated tubular probe is a placement and retrieval probe;

said placement and retrieval probe having an open first unattached tubular tip end and a second tubular end releasably attached to said lock assembly;

a fiber optic lens disposed adjacent said open first unattached tip end;

an optic fiber connected to said fiber optic lens and disposed within the wall and extending the length of said placement and retrieval probe to connect with a video pickup housed within said computerized base structure;

said fiber optic lens and said optic fiber providing visual indication on said display screen of the location of said open unattached tip end of said placement and retrieval probe as said placement and retrieval probe is inserted along the urethra of a patient under the control of a physician;

a custom designed reinforcement insert compressed and disposed within the lumen of said open unattached tip end of said placement and retrieval probe;

an elongated ram having a first end slidably extending through said locking assembly and said support housing and attached to said secondary movement carriage;

said elongated ram having a second end disposed within the lumen of said placement and retrieval probe and positioned in engagement with an end of said custom designed reinforcement insert; whereby said probe support housing is linearly moved along said fixed main track to insert said placement and retrieval probe into the urethra of the patient and position the open unattached tubular end thereof containing said custom designed reinforcement insert within the prostatic urethra of the patient.

11. The system of claim 10 including means for moving said probe support housing and said attached tubular portion of said placement and retrieval probe in such a manner relative to said elongated ram to push said reinforcement insert out of the lumen of said placement and retrieval probe, as the probe retreats from the prostate of the patient, thereby laying the reinforcement insert within the prostate of the patient;

said custom designed reinforcement insert expanding from the compressed condition as it emerges from the lumen of said placement and retrieval probe, under the impetus of said elongated ram, to the designed expanded condition to overcome any pressure being exerted on the prostatic urethra by the diseased prostate; and means for withdrawing said tubular portion of said placement and retrieval probe and said elongated ram from the patient to leave said reinforcement insert in place within the prostate of the patient.

12. The system of claim 11 wherein said custom designed reinforcement insert is a helix having a spindle shaped configuration and is constructed from a ribbon of material selected from the group of biocompatible materials consisting of stainless steel and polycarbonate plastics.

13. The system of claim 12 wherein said ribbon of material is provided with a flattened oval cross sectional area and wherein the ends of said helix are fused to remove any sharp edges.

14. A system for detecting, evaluating and treatment of prostate and urinary problems in a male human comprising:

a power driven instrument element including a physician controlled elongated tubular mapping probe;

said elongated tubular mapping probe having a first end for insertion within the penile urethra, through the voluntary sphincter adjacent the prostate, into the prostate urethra and adjacent to the involuntary sphincter at the bladder opening of a patient;

optical means disposed through, and having a lens disposed at said first end of said mapping probe to permit visual observations along the length of the urethra during movement of said first end of said placement and removal device along the urethra;

axial pressure sensor means disposed on said elongated tubular mapping probe to sense axial pressure resistance to movement of said elongated tubular mapping probe through the urethra of a patient;

radial pressure sensor means also disposed within said mapping probe to detect and measure radial pressure variables along the length of the prostate urethra during movement of said placement and removal device therealong;

said elongated tubular mapping probe having a second end releasably secured to a physician controllable, power driven, gear train housed within a base housing structure;

a computer driven display screen in circuit connection with said optical, axial pressure sensor and said radial pressure sensor means to provide optical data, as well as, axial and radial pressure data displays thereon;

means within said base housing structure and connected to said display screen to indicate pressures within the prostate in tubular form by location, dimension of the prostate and spatial relationship of the voluntary and involuntary sphincters; and recording means in circuit connection with said optical and said radial and said axial pressure sensor means to permanently record a patient profile of the pressure and dimensional data displayed on said display screen; whereby radial pressure data are produced in tabular form as a function of location along the urethra, axial pressure data show the force needed to overcome the resistance of the voluntary and involuntary sphincters and their geometric relationships, and said optical data may be compared with the same information taken by previous scans of the same patient and compared with similar data from any on-line data base available.

15. The system of claim 14 including a custom fabricated prostate reinforcement insert, said reinforcement insert being custom fabricated from the measured, visual and tabulated dimensional observations and by the data obtained from said optical, said radial and said axial pressure sensor and ultrasonic scan data means.

16. The system of claim 15 wherein said prostate reinforcement insert is constructed of a material selected from the group of materials consisting of biocompatible metals and biocompatible plastics; said material being shaped as a helix of ribbon having a flattened oval cross section and forming an elongated flexible spindle configuration wherein the diameter of a center length portion thereof exceeds the diameter of the ends.

17. A system for detecting, evaluating and treatment of prostate and urinary problems in a male human comprising:

a tubular probe means for detection of the presence of diseases and abnormalities of the prostate and urethra of a human male; p1 drive means releasably connected to said tubular probe means and controllable by a physician operator to insert said tubular probe means through the penile urethra, through the voluntary sphincter disposed between the penile urethra and the prostate urethra, into the prostate urethra to a position therein adjacent to the involuntary sphincter connecting the bladder to the prostatic urethra;

data collecting means carried by said tubular probe means;

computer means in operative connection with said data collection means for converting informational data received from said data collection means into visual images;

a display screen in operative connection with said computer means to receive and display the visual images of data from said computer means; and recording means in operative connection with said display screen to make a permanent record of the computer converted informational data displayed on said display screen.

18. The system of claim 17 wherein said data collecting means includes:

a radial pressure sensor, an axial pressure sensor, an ultrasonic scanner, and fiber optic means;

said radial pressure sensor serving to measure radial pressure variations along the insertion path of said tubular probe means through the prostate urethra;

said axial pressure sensor serving to measure axial pressures encountered as said tubular probe means encounters said voluntary sphincter and the path of movement through said prostatic urethra;

said ultrasonic scanner serving to provide tissue and density characterization throughout the volume of the prostate; and said fiber optic means permitting visual observation of the penile and prostatic urethras as said tubular probe is moved therealong.

19. The system of claim 17 wherein said data collecting means includes mapping and measurement instrumentation to accurately provide measurements of distance from the tip of the penis to the voluntary sphincter at the entrance to the prostate and an accurate distance measurement between said voluntary and said involuntary sphincters to thereby provide an accurate measurement of the prostate urethra length; the distance between said voluntary and said involuntary sphincters; and a visual and tabulated pressure map of the penile urethra, the prostate urethra, and said sphincters; and a tomographical type, volume map showing structures, both normal and abnormal, present within the prostate, their location, density and texture.

20. A method of detecting, evaluating and treatment of prostate and urinary problems in a male human comprising the steps of:
   providing a computerized base structure including a computer and controls therefor, a display screen and a data recording means;
   providing a fixed main movement track and a secondary movement carriage linearly movable along the main movement track;
   providing a probe support housing supported by an movable with the secondary movement carriage and independently and linearly movable relative to the secondary movement carriage;
   releasably securing an elongated tubular probe, adapted for insertion through the urethra of a male patient, to the probe support housing;
   providing an optic fiber connection from the computerized base structure to the tip end of the elongated tubular probe;
   inserting the tip end of the tubular elongated probe into the penile urethra of a male human patient;
   computer controlling movement of the probe support housing to gradually move the elongated tubular probe through the penile urethra, the voluntary sphincter, the prostatic urethra and, at least, to a point adjacent the involuntary sphincter leading from the bladder opening into the prostate urethra of a male patient;
   providing a lighted optical lens on the optic fiber connection at the tip end of the tubular elongated probe and in optical connection through the optic fiber with the display screen; and
   observing movement of the tubular elongated probe on the display screen through the lighted optical lens.

21. The method of claim 20 wherein the elongated tubular probe is a mapping probe and including the steps of providing axial and radial pressure data collecting apparatus within the body of the elongated tubular probe;
   converting the axial and radial pressure data collected into tabular form;
   displaying the visual images obtained from the optic fiber connection and the tabulated pressure data received from the axial and radial pressure data collecting apparatus onto the display screen to thereby provide a dimensional map of the penile and prostate urethras as well as the spatial relationship of the voluntary and involuntary sphincters; and
   recording the visual and tabulated data as a permanent profile record of the urethra and prostate of the patient.

22. The method of claim 20 wherein the elongated tubular probe is a tubular placement and retrieval probe; and including the steps of:
   providing a custom designed reinforcement insert for the prostate observed; providing the custom designed reinforcement insert of a spindle configuration to provide an enlarged diameter central insert area and reduced diameter ends; wherein,
   the enlarged diameter central insert area is designed to press against the prostate urethra wall with sufficient force to overcome any pressures exerted thereon by the diseased prostate and maintain the prostatic urethra open for flow of urine therethrough and the reduced diameter ends are disposed adjacent the voluntary and involuntary sphincters.

23. The method of claim 22 wherein the tubular placement and retrieval probe includes an elongated ram slidably positioned within the tubular portion thereof; and including the steps of:
   positioning the custom designed reinforcement insert within the open tip end of the tubular placement and retrieval probe;
   positioning a slidable ram within the opposite end of the tubular placement and retrieval probe wherein one end of the elongated slidable ram is spaced from the open tip end of the tubular placement and retrieval probe and the other end of the ram extends through the other end of the tubular placement and retrieval probe and is secured to the motor drive assembly;
   compressing and positioning the custom designed reinforcement insert into the open tip end of the placement and retrieval probe and against an end of the elongated slidable ram;
   employing the motor drive assembly to insert the placement and retrieval probe through the penile urethra into the prostate urethra while observing movement thereof to position the area housing the reinforcement insert completely within the prostate urethra and disposed between the voluntary sphincter and the involuntary sphincter;
   maintaining the reinforcement insert within the prostate by pressure from the elongated slidable ram while withdrawing the tubular placement and retrieval probe to lay the reinforcement insert in place within the prostate urethra; and thereafter,
   completely removing the tubular elongated placement and removal probe and elongated ram from the patient.

24. The method of claim 23 including providing a capture mechanism on a modified elongated slidable ram with the capture mechanism being in the form of a half turn, coarse threaded shaft removal tip disposed on the ram end spaced from the open tip end of the tubular placement and retrieval probe;
   providing a threaded receptacle within the open end of the reinforcement insert adjacent the voluntary sphincter;
   inserting the capture mechanism into the open end of the reinforcement insert;
   rotating the modified ram to threadingly capture the insert onto the modified ram;
   continuing rotation of the modified ram to rotate the helix of the reinforcement insert, while advancing the tubular probe tube at the same rate that the reinforcement insert is being moved to provide minimum friction both to the urethra walls and to the recompression of reinforcement insert back into the lumen of the placement and retrieval probe tube.

25. The method of claim 20 wherein the elongated tubular probe houses within the radial pressure sensing chamber, a radial ultrasonic transducer assembly to map the volume of the prostatic tissue;
   characterizing the configuration, location size, density, and texture of any and all normal and abnormal structures found therein;
   displaying said data in tomographical format onto the display screen to thereby provide the capability of detecting and diagnosing any malignant tissue contained therein; and recording the tomographical data as a permanent record of the malignancy or non-malignancy of the patient at that point in time.

26. A system for detecting, evaluating and treatment of prostate and urinary problems in a male human comprising:

mapping probe means for measuring radial and axial pressure and for ultrasonically scanning the volume of the prostatic capsule, and for optically viewing the interior of the urethra and bladder of a male human patient;

display means permitting visual inspection of the urethra as said mapping probe means measures the radial and axial pressure therealong;

recording means for making a permanent record of the radial and axial pressure measurements, as well as the ultrasonic and optical images made by said mapping probe means;

a reinforcement insert positionable within the prostatic urethra of the patient;

placement probe means for placing said reinforcement insert within the prostate urethra of the patient;

computer control means for inserting and withdrawal of said mapping probe means from within the prostatic urethra of the patient;

said computer control means including a probe support housing releasably connected to said mapping probe means during insertion and withdrawal thereof;

said placement probe means being releasably connected to said probe support housing after withdrawal of said mapping probe means from said patient and removal of said mapping probe from said probe support housing;

said placement probe means including a hollow outer tube and said reinforcement insert being compressed and retained within said hollow outer tube for placement thereof within the prostatic urethra;

ram means carried within said hollow outer tube of said placement probe means for forcing said compressed reinforcement insert out of said placement probe when said placement probe is inserted within the prostatic urethra of the patient.

27. The system of claim 26 including lubrication means for said elongated tubular mapping probe;

said lubrication means including a plurality of ports disposed in spaced relationship along the exterior surface of said elongated tubular mapping probe;

a plurality of tubular lubricant passageways disposed in spaced parallel relationship within said elongated tubular mapping probe;

an annular lubricant chamber disposed about said elongated tubular mapping probe adjacent said second end thereof;

each of said plurality of tubular lubricant passageways being in fluid communication with said annular lubricant chamber and with at least one of said ports; and a lubricant reservoir supported by said base housing structure and in fluid communication with and supplying lubricant to said annular lubricant chamber.

28. The system of claim 26 wherein said elongated tubular mapping probe includes an outer shell structure and an elongated hollow drive shaft contained within said outer shell structure;

said drive shaft having a first end rotatably extending through a first fixed bearing and connected to a drive gear disposed within said base housing;

said drive shaft having a second end rotatably extending through a second fixed bearing;

an elongated transducer housing having a first end secured to said second end of said drive shaft and a second end secured to a third bearing;

said third bearing being rotatably received within the nose portion of said elongated mapping probe;

a fluid filled chamber disposed within said tubular mapping probe; and said elongated transducer housing being contained within said fluid filled chamber.

29. The system of claim 28 including an ultrasonic scanning transducer disposed within said transducer housing;

an air backed acoustic mirror also contained within said transducer housing and in linear spaced alignment with said ultrasonic scanning transducer;

a curvature control for said acoustic mirror provided within said transducer housing; and means within said outer shell structure of said elongated mapping probe permitting acoustic vibration over the radius thereof housing said fluid filled chamber.

30. The system of claim 29 wherein said means within said outer shell structure of said elongated mapping probe permitting acoustic vibration over the radius thereof housing said fluid filled chamber includes, a pair of circumferential exterior creases provided within the outer shell; said circumferential exterior creases being spaced to define the length of the fluid filled chamber therebetween: and, at least one longitudinal crease provided along the length of said mapping probe between said pair of circumferential exterior creases.

31. The system of claim 29 including means for providing a controlled oscillating, rotative movement, through said drive shaft, to said transducer housing contained within said fluid filled chamber.

32. The system of claim 29 including:

a first pressure tube extending along a length of said mapping probe;

a first pressure transducer disposed on and supported by said base housing;

said first pressure tube providing fluid communication between said fluid filled chamber and said first pressure transducer;

a second pressure tube extending along the length of said mapping probe;

a transparent fluid filled diaphragm disposed at the tip end of said mapping probe;

a second pressure transducer disposed on and supported by said base housing;

second pressure tube providing fluid communication between said transparent fluid filled lens and said second pressure transducer;

whereby radial pressure variations are hydraulically transferred to said first pressure transducer as said mapping probe moves along the urethra and, simultaneously therewith, axial pressure is indicated from said transparent pressure diaphragm to said second pressure transducer, with the output of said first and said second pressure transducers being converted into numerical readings that are displayed on said display screen.

33. The system of claim 29 wherein the fluid contained within said fluid filled chamber and within said transparent fluid filled diaphragm is distilled water.

34. The system of claim 33 including a one way valve disposed within said reinforcement insert;
   said one way valve including an annular ring secured within said reinforcement insert downstream from and adjacent the involuntary sphincter of the patient;
   a plurality of conical shaped, resilient, depending petals extending downstream from said annular ring;
   said petals flexing to permit flow from the bladder of the patient into the reinforcement insert and through the prostatic urethra but resiliently closing to prevent retrograde flow from the prostatic urethra into the bladder.

35. The system of claim 33 including a one way rotary valve;
   said rotary valve having a valve housing secured within, and having an external diameter substantially equal to, the internal diameter of said reinforcement insert;
   a drive gear rotatably disposed within said valve housing;
   a drive shaft having a fixed gear thereon and meshing with said drive gear;
   a rotary valve disc secured to said drive shaft and rotatably driven in one direction by said drive gear acting on said fixed gear;
   a pawl actuated by muscular control of the patient to effect incremental rotation of said drive gear;
   a fixed web disposed within said rotary valve housing;
   said fixed web and said rotary valve disc each being provided with a plurality of equal size and number of spaced openings therethrough; whereby,
   when the spaced openings in said fixed web are aligned with the spaced openings in said rotary valve disc, fluid flow is permitted through said rotary valve and said reinforcement insert and, when the spaced openings in said fixed web and the spaced openings in said rotary valve disc are not in alignment, no flow is permitted through said rotary valve and the reinforcement insert.

36. The system of claim 35 wherein said pawl is in the form of a compression ring and disposed externally, relative to said reinforcement insert and, against the prostatic urethra of the patient;
   said compression ring having an extending tip end protruding through the body of said reinforcement insert and engaging a space between two teeth on said drive gear; whereby,
   inwardly directed radial pressure on said compression ring, applied by patient voluntary contraction of the bladder, as normally exerted during voluntary urination; collapses said compression ring and pushes said extending tip inward to effect rotation of said drive gear and resulting rotation of said rotary disc and to cause alignment, or to remove from alignment, the spaced openings in said fixed web and said rotary valve disc.

37. A system for detecting, evaluating and treatment of prostate and urinary problems in a human male patient comprising:
   a first elongated probe for insertion through the urethra of a patient from the tip of the penis into the bladder;
   computer control means operable by a physician to control the rate and distance of movement of said first probe into and out of the patient;
   said first elongated probe including lighted optical viewing means, axial pressure measuring means, radial pressure measuring means, and ultrasonic scanning means;
   display and recording means in operative connection with said first elongated probe to provide a visual and tabular display of the visual and pressure data acquired by said optical viewing means, said axial, said radial pressure measuring means, and said ultrasonic scanning means;
   a reinforcement insert custom designed from the data observed and recorded by said display and recording means;
   said reinforcement insert having a spindle configuration with an enlarged diameter central area and reduced diameter ends and designed to overcome any excess radial pressure being exerted on the prostatic urethra by a diseased prostate to retain the prostatic urethra at a normal diameter; and
   a second elongated probe means for inserting said reinforcement insert into the urethra of the patient and for laying said reinforcement insert in place within the prostatic urethra.

38. The system of claim 37 including removal means for removal of said reinforcement insert from the prostate of the patient;
   said removal means including said second elongated probe being provided with an outer tubular shell;
   an elongated ram slidably received within said outer shell;
   an insert capture mechanism disposed on a tip end of said elongated ram;
   said insert capture mechanism comprising a half turn, coarse threaded, shaft removal tip portion, and a threaded receptacle formed in an end of said reinforcement insert disposed adjacent the voluntary sphincter of the patient;
   means providing for rotation and linear movement of said elongated ram to engage and insert the half turn, coarse threaded, shaft removal tip within the threaded receptacle formed in said reinforcement insert to capture said reinforcement insert; and
   means for advancing said tubular shell of said second elongated probe while continuing rotation of said elongated ram and said captured reinforcement insert to recompress said reinforcement insert back into the lumen of said second probe.

39. The system of claim 37 wherein said reinforcement insert is constructed of a material selected from the group of materials consisting of biocompatible metals and biocompatible plastics;
   said material being a helix of a flattened oval cross section ribbon, provided with fused ends, and shaped in the form of a spindle;
   said reinforcement insert including removable radiation pellets embedded therein to treat a tumor of the prostate; and
   means on said reinforcement insert to facilitate removal of said reinforcement insert from the patient.

40. Reinforcement means for placement within a fluid conduit in a human patient to provide support, and to relieve pressure on, the walls of the conduit, comprising:
   a spindle shaped reinforcement insert;

said reinforcement being formed of a helix of ribbon and provided with an enlarged diameter central area and reduced diameter ends;

said spindle shaped helix of ribbon having a flattened oval cross sectional area and formed of a biocompatible material; and said biocompatible material being selected from the group of biocompatible materials consisting of metals and plastics.

41. The reinforcement means of claim 40 wherein said biocompatible material is stainless steel.

42. The reinforcement means of claim 40 wherein said biocompatible material is a polycarbonate.

43. The reinforcement means of claim 40 wherein said reinforcement insert is positioned within the prostatic urethra of a male human patient and designed to relieve pressure being exerted on the prostatic urethra by a diseased prostate; and, wherein said reduced diameter ends of said reinforcement insert are both contained within the prostatic urethra.

44. The reinforcement means of claim 43 including a one-way valve disposed within said reinforcement insert;

said one way valve including an annular ring secured within said reinforcement insert downstream from and adjacent the involuntary sphincter of the patient; and a plurality of conical shaped, resilient, depending petals extending downstream from said annular ring; wherein said depending petals flex to open and permit normal flow from the bladder of the patient into the prostatic urethra but resiliently close to prevent retrograde flow of fluid from the prostatic urethra into the bladder.

45. The reinforcement means of claim 40 wherein said reinforcement insert is positioned within the prostate of a male human patient; said reinforcement insert having one end thereof extending through the prostatic urethra into the bladder of the patient to relieve pressure and maintain open the involuntary sphincter at the opening of the bladder that previously was obstructed from an occludent flap resulting from an extremely enlarged Benign Prostatic Hyperplasia; and, valve means disposed within said reinforcement insert to permit patient control of urine flow from the bladder.

46. The reinforcement means of claim 45 wherein said valve means includes:

a valve housing secured within the inside diameter of said reinforcement insert;

a drive gear rotatably disposed within said valve housing;

a drive shaft having a fixed gear thereon and meshing with said drive gear;

a rotary valve disc secured to said drive shaft and rotatably driven in one direction by said drive gear acting on said fixed gear thereon;

a pawl actuated by muscular control of the patient to effect incremental rotation of said drive gear;

a fixed web disposed within said rotary valve housing;

said fixed web and said rotary valve disc each being provided with a plurality of equal size and number of spaced openings therethrough; whereby, when the spaced openings in said fixed web are aligned with the spaced openings in said rotary valve disc, fluid flow is permitted through said rotary valve and said reinforcement insert and, when the spaced openings in said fixed web and the spaced openings in said rotary valve disc are not in alignment, no flow is permitted through said rotary valve and said reinforcement insert.

47. The reinforcement means of claim 46 wherein said pawl is in the form of a compression ring and disposed externally, relative to said reinforcement insert and, against the prostatic urethra of the patient;

said compression ring having an extending tip end protruding through the body of said reinforcement insert;

said extending tip end engaging a space between two teeth on said drive gear; whereby, inwardly directed radial pressure on said compression ring, applied by patient voluntary contraction of the bladder, as normally exerted during voluntary urination; collapses said compression ring and pushes said extending tip end inward to effect rotation of said drive gear, and resulting rotation of said rotary disc, to cause alignment, or removal from alignment, of the spaced openings in said fixed web and said rotary valve disc.

48. The reinforcement means of claim 40 including a piezo-electric valve;

said piezo-electric valve having a valve housing secured within said reinforcement insert;

a fixed web secured within said valve housing;

said fixed web having a semi-circular opening therethrough;

a rotary disc valve disposed within said valve housing adjacent said fixed web;

said rotary disc valve being also provided with a semi-circular opening;

a piezo-electric element secured to and adapted to impart rotation to said rotary disc valve when subjected to an electric pulse;

said rotary disc valve being movable by said piezo-electric element from a closed first position, wherein the semi-circular opening therein is disposed 180 degrees from the semi-circular opening in said web, to an open second position, wherein the semi-circular openings in said rotary disc and said web are in alignment to permit fluid flow therethrough, and control means for actuating said piezo-electric element to effect controlled rotation of said rotary disc valve.

49. The reinforcement means of claim 48 wherein said control means for actuating said piezo-electric element includes a pair of small insulated wires extending from said piezo-electric element to a control unit operable by the patient.

* * * * *